United States Patent
Wong et al.

(10) Patent No.: US 9,919,059 B2
(45) Date of Patent: Mar. 20, 2018

(54) MULTISTAGE NANOPARTICLE DRUG DELIVERY SYSTEM FOR THE TREATMENT OF SOLID TUMORS

(71) Applicants: Massachusetts Institute of Technology, Cambridge, MA (US); The Massachusetts General Hospital, Boston, MA (US)

(72) Inventors: Cliff R. Wong, Cambridge, MA (US); Moungi G. Bawendi, Cambridge, MA (US); Dai Fukumura, Newton, MA (US); Rakesh K. Jain, Wellesley, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/102,118

(22) Filed: Dec. 10, 2013

(65) Prior Publication Data

US 2014/0161884 A1  Jun. 12, 2014

Related U.S. Application Data

(60) Provisional application No. 61/735,168, filed on Dec. 10, 2012.

(51) Int. Cl.
| | |
|---|---|
| *A61K 9/14* | (2006.01) |
| *A61K 47/48* | (2006.01) |
| *A61K 47/62* | (2017.01) |
| *A61K 47/56* | (2017.01) |
| *A61K 47/64* | (2017.01) |
| *A61K 47/55* | (2017.01) |
| *A61K 47/50* | (2017.01) |

(52) U.S. Cl.
CPC .. *A61K 47/48915* (2013.01); *A61K 47/48338* (2013.01); *A61K 47/48892* (2013.01); *A61K 47/50* (2017.08); *A61K 47/55* (2017.08); *A61K 47/56* (2017.08); *A61K 47/62* (2017.08); *A61K 47/64* (2017.08); *A61K 47/641* (2017.08)

(58) Field of Classification Search
None
See application file for complete search history.

(56) References Cited

U.S. PATENT DOCUMENTS

| | | | |
|---|---|---|---|
| 5,871,710 A * | 2/1999 | Bogdanov | A61K 47/48169 424/1.65 |
| 7,498,035 B2 * | 3/2009 | Ji et al. | 424/181.1 |
| 8,110,179 B2 | 2/2012 | Cheng | |
| 2005/0048650 A1 * | 3/2005 | Ignatious | A61K 9/127 435/458 |
| 2010/0298495 A1 | 11/2010 | Bobe | |
| 2011/0166063 A1 * | 7/2011 | Bossard | A61K 47/48215 514/5.9 |

FOREIGN PATENT DOCUMENTS

WO  200647703  5/2006

OTHER PUBLICATIONS

Chang, et al., "Formulation of functionalized PLGA-PEG nanoparticles for in vivo targeted drug delivery", Biomaterials, 28: 869-76 (2007).
Yokoyama, et al., "Preparation of micelle-forming polymer-drug conjugates", Bioconj. Chem., 3: 295-301 (1992).

* cited by examiner

*Primary Examiner* — James W Rogers
(74) *Attorney, Agent, or Firm* — Pabst Patent Group LLP

(57) ABSTRACT

Nanoparticles for a selective, two stage delivery to tumors have been developed. The nanoparticles are initially sized so that they preferentially accumulate in the tumor tissue as a result of leakage through the defective vascular in the solid tumors. Once in the tumor tissue, the nanoparticles are cleaved hydrolytically and/or by enzymatic cleavage over time to release smaller nanoparticles carrying therapeutic, prophylactic or diagnostic agents into the necrotic interior of the tumors. This provides a simple, elegant and highly effective means of delivery drug selectively not just to tumors generally, but, more importantly, into the poorly vascularized necrotic interiors which drugs are normally unable to penetrate. The nanoparticles have a number of advantages: less toxicity due to selective accumulation only in the tumors; access into the poorly vascularized necrotic interiors of the tumor; and sustained release over a period of time within the tumor.

26 Claims, 4 Drawing Sheets

MULTISTAGE NANOPARTICLE DRUG DELIVERY SYSTEM FOR THE TREATMENT OF SOLID TUMORS

CROSS REFERENCE TO RELATED APPLICATION

This application claims benefit of and priority to U.S. Provisional Application No. 61/735,168, filed Dec. 10, 2012, all of which is incorporated by reference in its entirety.

STATEMENT REGARDING FEDERALLY SPONSORED RESEARCH OR DEVELOPMENT

This invention was made with government support under Agreement Nos. R01-CA126642, R01-CA085140, R01-CA115767, R01-CA080124, and R01-CA096915 awarded by the National Institutes of Health, and Agreement No. W81XWH-10-1-0016 awarded by the U.S. Department of Defense Breast Cancer Research Program. The government has certain rights in the invention.

FIELD OF THE INVENTION

The present invention relates to polymer-drug conjugates used to form nanoparticles for the multistage delivery of therapeutic agents to solid tumors, as well as compositions containing the conjugates, methods of making the conjugates, and methods of using the conjugates for treating solid tumors.

BACKGROUND OF THE INVENTION

Despite advancements made in treatment and diagnosis, cancer remains the second leading cause of mortality in the United States, superseded only by heart disease. Solid tumors account for more than 85% of cancer mortality. Currently, the primary treatment modality for solid tumors is cytoreductive surgery followed by adjuvant chemotherapy and/or radiotherapy. While this strategy has been successfully employed in a number of patients, it is accompanied by cytotoxicity to normal cells and tissues, and the development of multidrug resistance (MDR).

Targeted cancer therapies offer the potential to improve the treatment of solid tumors. By targeting therapeutic agents to solid tumors, cytotoxicity to normal cells and tissues may be minimized. In addition, targeted therapies provide the opportunity to more rigorously control the concentration of therapeutic agent at the site of a tumor, potentially limiting the emergence of drug resistance.

Nanoparticles (NPs) have been explored for the targeted delivery of therapeutic agents to solid tumors. The larger size of nanoparticles, as compared to conventional small molecule cancer therapeutics, allows them to preferentially accumulate in solid tumors by the enhanced permeability and retention (EPR) effect. The EPR effect is a consequence of the abnormal vasculature frequently associated with solid tumors. The vasculature of tumors is typically characterized by blood vessels containing poorly-aligned defective endothelial cells with wide fenestrations. As a result, nanoparticles with an average particle size of between about 100 nm to 200 nm can preferentially extravasate out of the leaky regions of the tumor vasculature, and accumulate within the solid tumor. In addition, the lack of lymphatics in the tumor region prevent the nanoparticles from being efficiently filtered and removed, increasing the residence time of the nanoparticles within the tumor relative to residence in normal tissue and the vasculature.

In view of the potential of nanoparticles to passively target therapies via the EPR effect, nanoparticle formulations have been investigated for the delivery of small molecule therapeutic agents to solid tumors, including two FDA-approved nanoparticle-based therapeutics—DOXIL® (an 100 nm PEGylated liposomal form of doxorubicin) and ABRAXANE® (an 130 nm albumin-bound paclitaxel nanoparticle). While these formulations exhibit improved pharmacokinetic properties and reduced adverse effects, existing nanoparticle formulations have provided only modest survival benefits. The limited efficacy of these existing nanoparticle formulations stems from their inability to effectively deliver the therapeutic agents throughout the solid tumor.

Systemic delivery of therapeutic agents to solid tumors is a three step process: (1) blood-borne delivery of the therapeutic agent to different regions of the tumor; (2) transport of the therapeutic agent across the vessel wall into the solid tumor; and (3) passage of the therapeutic agent from the tumor tissue adjacent to the vasculature to the tumor cells via diffusion through the interstitial space.

Abnormalities in the tumor vasculature lead to highly heterogeneous vascular perfusion throughout solid tumors. While the microvascular density is often high at the invasive edge of tumors, the tumor center is often unperfused. As a result, diffusion through the interstitial matrix is the primary mode for drug transport to the poorly perfused tumor center and the nanoparticles are unable to effectively diffuse through the dense interstitial matrix of the solid tumor—a complex assembly of collagen, glycosaminoglycans, and proteoglycans—to reach the tumor cells within the tumor center.

As a consequence, existing nanoparticle formulations are limited in their ability to deliver a therapeutic agent throughout the entire tumor. For example, in the case of DOXIL®, upon accumulation in a solid tumor via the EPR effect, the liposomal particles are unable to diffuse through the dense interstitial matrix of the tumor and remain trapped close to the tumor vasculature. The liposomes trapped near the vasculature release doxorubicin; however, in spite of its relatively low molecular weight (approximately 400 Da), the doxorubicin cannot migrate far from the particles due to avid binding to DNA and sequestration in acidic endosomes of perivascular tumor cells.

As a consequence, existing nanoparticle formulations tend to produce heterogeneous therapeutic effects in solid tumors. The nanoparticle formulations deliver an effective amount of the therapeutic agent near the surface of the tumor where the leaky vasculatures are located; however, effective amounts of the therapeutic agents are not delivered to the cells in the tumor center. This is particularly problematic because the hostile microenvironment of the tumor center (characterized by low pH and low $pO_2$) often harbors the most aggressive tumor cells. As a result, the tumor will regenerate if the cells in the tumor center are not eliminated. Moreover, exposure of the tumor cells to a sublethal concentration of the therapeutic agent can facilitate the development of drug resistance in the remaining cell lines. As a result, existing nanoparticle formulations have thus far provided only modest survival benefits when used to treat solid tumors.

Therefore, it is an object of the invention to provide improved formulations for the targeted treatment of solid tumors.

It is also an object of the invention to provide polymer-drug conjugates capable of delivering an effective amount of one or more active agents to tumor cells throughout the solid tumor.

It is a further object of the invention to provide improved methods of treating solid tumors, including malignant tumors.

SUMMARY OF THE INVENTION

Polymeric nanoparticles for delivery of one or more drugs to solid tumors are provided for size-targeted, two stage delivery. Initially, the nanoparticles possess an average particle size that allows them to preferentially extravasate from the leaky regions of the tumor vasculature and accumulate within the perivascular tumor tissue via the EPR effect. Once the nanoparticles have extravasated into the tumor tissue, the nanoparticles release one or more smaller nanoparticles having an average particle size and surface chemistry which significantly lowers their diffusional hindrance in the interstitial matrix. As a result, the smaller nanoparticles are able to efficiently penetrate into the tumor parenchyma. The smaller nanoparticles contain one or more therapeutic, prophylactic or diagnostic agents that are released as the smaller nanoparticles diffuse deep into the tumor.

The nanoparticles are formed from one or more polymer-drug conjugates. In some instances, the polymer-drug conjugate is defined by Formula I

Formula I

In some embodiments of Formula I, A is a small molecule anti-neoplastic agent. The one or more drugs can optionally be connected to the hydrophilic polymer segment by means of a spacer. In some embodiments, the spacer is an alkyl group, an alkylaryl group, an oligo- or polyethylene glycol chain, or an oligo- or poly(amino acid) chain. The spacer can includes one or more heteroatoms, one or more cleavable subunits, such as an oligo- or poly(peptide) that can be enzymatically cleaved, and/or one or more hydrolysable functional groups, such as an ester or amide.

The hydrophilic polymer segment can be any biocompatible hydrophilic homopolymer or copolymer. In some embodiments, the hydrophilic polymer segment is a graft copolymer containing a polymeric backbone functionalized by one or more hydrophilic polymeric side chains. In some embodiments, the hydrophilic polymer segment is a graft copolymer containing a poly-glutamic acid backbone functionalized by one or more poly(ethylene glycol) (PEG) side chains. In some embodiments, the poly-glutamic acid backbone is poly-L-glutamic acid. In some embodiments, the hydrophilic polymer is not gelatin.

The hydrophobic polymer segment can be any biocompatible hydrophobic polymer or copolymer. In some embodiments, the hydrophobic polymer segment is a biodegradable aliphatic polyester. In particular embodiments, the hydrophobic polymer segment is poly(lactic acid), poly(glycolic acid), or poly(lactic acid-co-glycolic acid).

In some embodiments, the polymer-drug conjugate is defined by Formula II

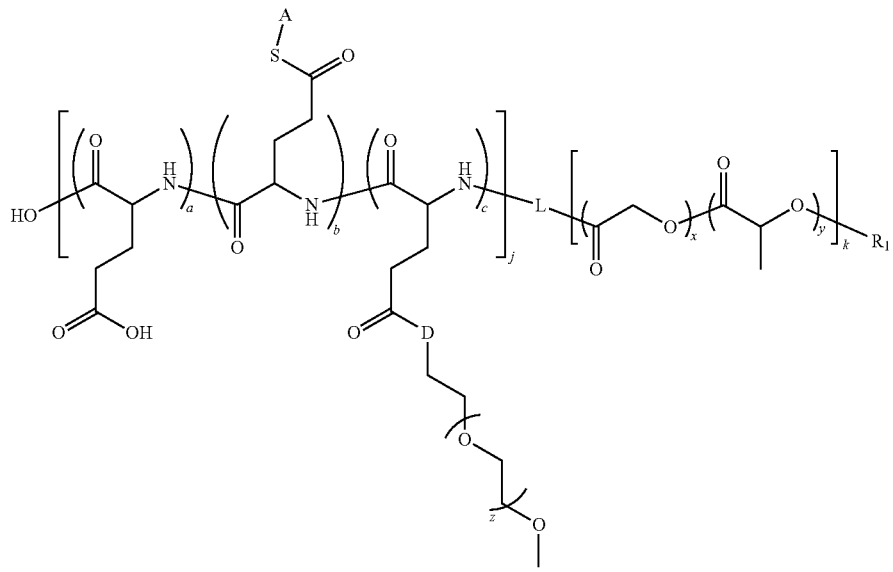

Formula II wherein
A is, independently for each occurrence, a drug;
S is absent, or is a spacer group;
X is a hydrophilic polymer segment;
L is absent, or is a linking group;
Y is a hydrophobic polymer segment; and
b is an integer between 1 and 100.

wherein
A is a drug;
S is absent, or is a spacer group;
L is absent, or is a linking group;
D is, independently for each occurrence, O, S, or $NR_1$;
$R_1$ is H or a $C_1$-$C_{12}$ alkyl group optionally containing between one and six oxygen heteroatoms;

a, b, c, and d are each, independently, an integer between 1 and 1000, more preferably between 1 and 500, most preferably between 1 and 100;

x and y are each, independently, an integer between 1 and 1000, more preferably between 1 and 500, most preferably between 1 and 100;

z is, independently for each occurrence, an integer between 1 and 1000, more preferably between 1 and 500, most preferably between 1 and 100; and j and k are each, independently, an integer between 1 and 1000, more preferably between 1 and 500.

In some embodiments of Formula II, A is a small molecule anti-neoplastic agent. In some embodiments, A is an anthracycline, such as doxorubicin or daunorubicin, or a topoisomerase inhibitor, such as camptothecin.

In some embodiments of Formula II, S is absent. In other embodiments, S is an alkyl group, an alkylaryl group, an oligo- or polyethylene glycol chain, or an oligo- or poly(amino acid) chain. S can include one or more heteroatoms and/or one or more hydrolysable functional groups, such as an ester or amide.

In some embodiments of Formula II, D is, independently for each occurrence, O or NH. In some embodiments, D is, in every occurrence, O. In still other embodiments, D is, in every occurrence, NH.

In some embodiments of Formula II, L is absent. In other embodiments, L is a cleavable linker which is designed to be cleaved in response to an endogenous stimulus characteristic of the tumor microenvironment, such as a change in pH or the presence of an enzyme. The linker may include one or more hydrolysable functional groups, such as an ester, amide, or glycosidic bond, which can be hydrolyzed in acidic conditions. The linker can include an oligo- or poly(peptide) sequence designed to be cleaved by a matrix metalloproteinases (MMPs), such as matrix metalloproteinase-2 (MMP-2) or matrix metalloproteinase-9 (MMP-9). The can linker also includes an oligo- or poly(peptide) sequence designed to be cleaved by a cathepsin, such as Cathepsin B. The linker can include an oligo- or poly(peptide) sequence designed to be cleaved by autotaxin.

In other embodiments, the hydrophobic polymer segment, along with an optional linking group, is grafted onto the backbone of the hydrophilic polymer segment. In one embodiment, the polymer-drug conjugate is defined by Formula III

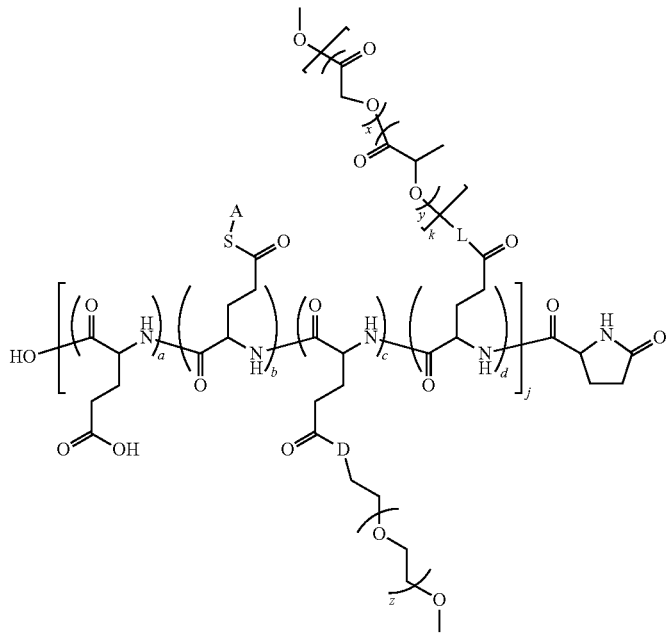

Formula III wherein

A is a drug;

S is absent, or is a spacer group;

L is absent, or is a linking group;

D is, independently for each occurrence, O, S, or $NR_1$;

$R_1$ is H or a $C_1$-$C_{12}$ alkyl group optionally containing between one and six oxygen heteroatoms;

a, b, c, and d are each, independently, an integer between 1 and 1000, more preferably between 1 and 500, most preferably between 1 and 100;

x and y are each, independently, an integer between 1 and 1000, more preferably between 1 and 500, most preferably between 1 and 100;

z is, independently for each occurrence, an integer between 1 and 1000, more preferably between 1 and 500, most preferably between 1 and 100; and j and k are each, independently, an integer between 1 and 1000, more preferably between 1 and 500.

In some embodiments of Formula III, A is a small molecule anti-neoplastic agent. In particular embodiments, A is an anthracycline, such as doxorubicin or daunorubicin, or a topoisomerase inhibitor, such as camptothecin.

In some embodiments of Formula III, S is absent. In other embodiments, S is an alkyl group, an alkylaryl group, an oligo- or polyethylene glycol chain, or an oligo- or poly(amino acid) chain. S can include one or more heteroatoms and/or one or more hydrolysable functional groups, such as an ester or amide.

In some embodiments of Formula III, D is, independently for each occurrence, O or NH. In some embodiments, D is, in every occurrence, O. In still other embodiments, D is, in every occurrence, NH.

In some embodiments of Formula III, L is absent. In other embodiments, L is a cleavable linker which is designed to be cleaved in response to an endogenous stimulus characteristic of the tumor microenvironment, such as a change in pH or the presence of an enzyme. The linker may include one or more hydrolysable functional groups, such as an ester, amide, or glycosidic bond, which can be hydrolyzed in acidic conditions. The linker can include an oligo- or poly(peptide) sequence designed to be cleaved by a matrix metalloproteinases (MMPs), such as matrix metalloproteinase-2 (MMP-2) or matrix metalloproteinase-9 (MMP-9). The can linker also includes an oligo- or poly(peptide) sequence designed to be cleaved by a cathepsin, such as Cathepsin B. The linker can include an oligo- or poly(peptide) sequence designed to be cleaved by autotaxin.

In other embodiments, the polymer conjugate is defined by Formula IV

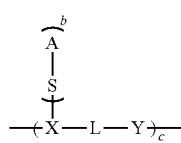

Formula IV wherein

A is, independently for each occurrence, a drug;

S is absent, or is a spacer group;

X is a hydrophilic polymer segment;

L is absent, or is a linking group;

Y is a poly(alkylene oxide) or copolymer thereof; and b and c are, independently, integers between 1 and 100.

In some embodiments of Formula IV, A is a small molecule anti-neoplastic agent. The one or more drugs can optionally be connected to the hydrophilic polymer segment by means of a spacer, S. In some embodiments, S is an alkyl group, an alkylaryl group, an oligo- or polyethylene glycol chain, or an oligo- or poly(amino acid) chain. S can includes one or more heteroatoms, one or more cleavable subunits, such as a oligo- or poly(peptide) that can be enzymatically cleaved, and/or one or more hydrolysable functional groups, such as an ester or amide.

The hydrophilic polymer segment can be any biocompatible hydrophilic homopolymer or copolymer. In some embodiments, the hydrophilic polymer segment is a graft copolymer containing a polymeric backbone functionalized by one or more hydrophilic polymeric side chains. In some embodiments, the hydrophilic polymer segment is a graft copolymer containing a poly-glutamic acid backbone functionalized by one or more poly(ethylene glycol) (PEG) side chains. In some embodiments, the poly-glutamic acid backbone is poly-L-glutamic acid.

Y can be any suitable poly(alkylene oxide) or copolymer thereof. In certain embodiments, Y is PEG, or a copolymer thereof.

In some embodiments, the polymer-drug conjugate is defined by Formula V

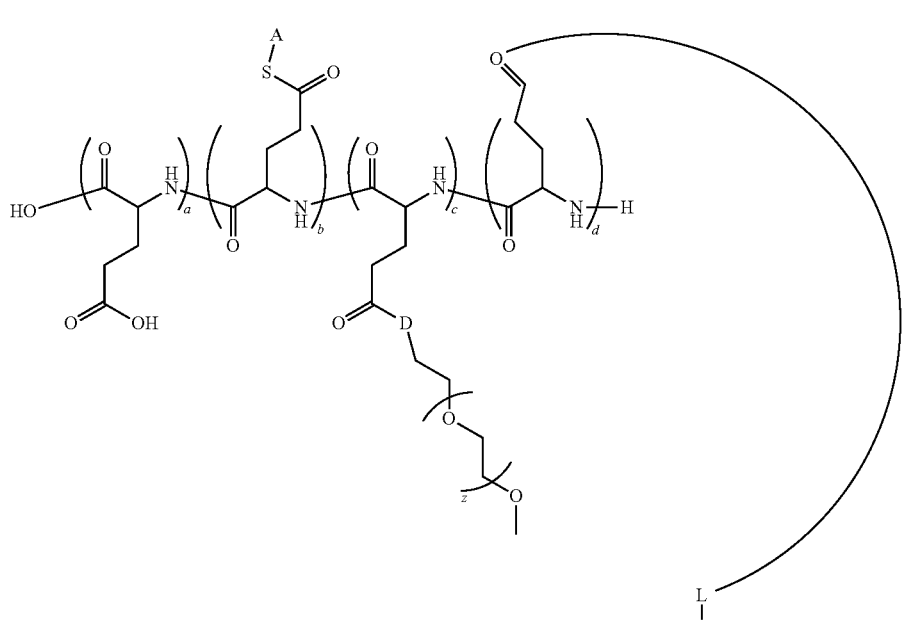

Formula V

-continued

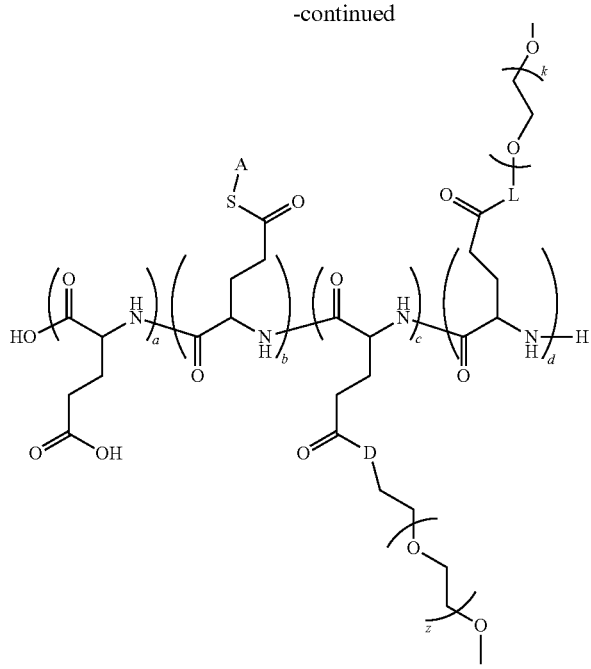

wherein
A is a drug;
S is absent, or is a spacer group;
L is absent, or is a linking group;
D is, independently for each occurrence, O, S, or $NR_1$;
$R_1$ is H or a $C_1$-$C_{12}$ alkyl group optionally containing between one and six oxygen heteroatoms;
a, b, c, and d are each, independently, an integer between 1 and 1000, more preferably between 1 and 500, most preferably between 1 and 100;
z is, independently for each occurrence, an integer between 1 and 1000, more preferably between 1 and 500, most preferably between 1 and 100; and
k is an integer between 1 and 1000, more preferably between 1 and 500.

In some embodiments of Formula V, A is a small molecule anti-neoplastic agent. In particular embodiments, A is an anthracycline, such as doxorubicin or daunorubicin, or a topoisomerase inhibitor, such as camptothecin.

In some embodiments of Formula V, S is absent. In other embodiments, S is an alkyl group, an alkylaryl group, an oligo- or polyethylene glycol chain, or an oligo- or poly(amino acid) chain. S can include one or more heteroatoms and/or one or more hydrolysable functional groups, such as an ester or amide.

In some embodiments of Formula V, D is, independently for each occurrence, O or NH. In some embodiments, D is, in every occurrence, O. In still other embodiments, D is, in every occurrence, NH.

In some embodiments of Formula V, L is absent. In other embodiments, L is a cleavable linker which is designed to be cleaved in response to an endogenous stimulus characteristic of the tumor microenvironment, such as a change in pH or the presence of an enzyme. The linker may include one or more hydrolysable functional groups, such as an ester, amide, or glycosidic bond, which can be hydrolyzed in acidic conditions. The linker can include an oligo- or poly(peptide) sequence designed to be cleaved by a matrix metalloproteinases (MMPs), such as matrix metalloproteinase-2 (MMP-2) or matrix metalloproteinase-9 (MMP-9). The can linker also includes an oligo- or poly(peptide) sequence designed to be cleaved by a cathepsin, such as Cathepsin B. The linker can include an oligo- or poly(peptide) sequence designed to be cleaved by autotaxin.

Nanoparticles can be formed from one or more polymer-drug conjugates using any suitable method known in the art. In some embodiments, the nanoparticles are formed by nanoprecipitation. In some instances, the nanoparticles generally contain a hydrophobic core, formed from hydrophobic polymer segments, and a hydrophilic shell composed of small nanoparticles formed from the hydrophilic polymer segments. In other instances, the nanoparticles are formed from a series of small nanoparticles joined by polymer segments to form a larger nanoparticle.

The nanoparticles have an average particle size that causes the nanoparticles to preferentially accumulate within the perivascular tumor tissue via the EPR effect. In some embodiments, the nanoparticles have an average particle size of between about 80 nm and about 500 nm, more preferably between about 100 nm and about 250 nm, most preferably between about 100 nm and about 200 nm. In other embodiments, the nanoparticles have an average particle size of between about 10 nm and about 50 nm, more preferably between about 10 nm and about 30 nm. Preferably, the nanoparticles exhibit or present significant amounts of a hydrophilic biocompatible polymer, such as PEG, on their surface to ensure biocompatibility and sufficient circulation time in vivo.

Once the nanoparticles have extravasated into the tumor tissue, the nanoparticles release one or more smaller nanoparticles. Preferably, the release of the one or more smaller nanoparticles is triggered by an endogenous stimulus characteristic of the tumor microenvironment, such as a change in pH and/or the presence of an enzyme such as MMP-2 which is present in elevated amounts in many tumors.

The smaller nanoparticles possess an average particle size and surface chemistry which significantly lowers their diffusional hindrance in the interstitial matrix. In some embodiments, the smaller nanoparticles have an average particle size of between about 1 nm and about 20 nm, more preferably between about 2 nm and about 15 nm, most preferably between about 4 nm and about 8 nm.

In some embodiments, the smaller nanoparticles contain significant amounts of a hydrophilic biocompatible polymer, such as PEG, on their surface which allows them to diffuse smoothly in the interstitial matrix, reducing the binding, sequestration, and metabolism that hinders the transport of much smaller therapeutic agents.

Also provided are pharmaceutical formulations containing multistage nanoparticles formed from one or more polymer-drug conjugates, as well as methods of administering these pharmaceutical compositions to treat or prevent solid tumors, including benign and malignant tumors. These formulations can effectively deliver therapeutic levels of one or more drugs throughout a solid tumor in an effective amount to slow tumor growth, halt tumor growth, or decrease tumor size.

BRIEF DESCRIPTION OF THE DRAWINGS

FIG. 1A illustrates that multistage nanoparticles of this type can be prepared from suitable polymer-drug conjugates by nanoprecipitation. As shown in FIG. 1B, upon hydrolysis, these multistage nanoparticles release a plurality of smaller nanoparticles which can penetrate the tumor interior. The drug is released from these smaller nanoparticles within the tumor interior by hydrolysis.

FIG. 2A illustrates that multistage nanoparticles of this type can be prepared from suitable polymer-drug conjugates containing cleavable linking groups by nanoprecipitation. As shown in FIG. 2B, upon cleavage of the linking group, such as by a suitable enzyme, these multistage nanoparticles release a plurality of smaller nanoparticles which can penetrate the tumor interior. The drug is released from these smaller nanoparticles within the tumor interior by hydrolysis.

FIG. 5A is a plot showing the percent of QD release from QDGelNPs as a function of time (in hours) following incubation with 230 nm (0.16 µM) MMP-2. FIG. 5B is a plot showing the percent of QD release from QDGelNPs as a function of MMP-2 concentration (in ng) following incubation for 12 hours.

DETAILED DESCRIPTION OF THE INVENTION

Figure 1A:
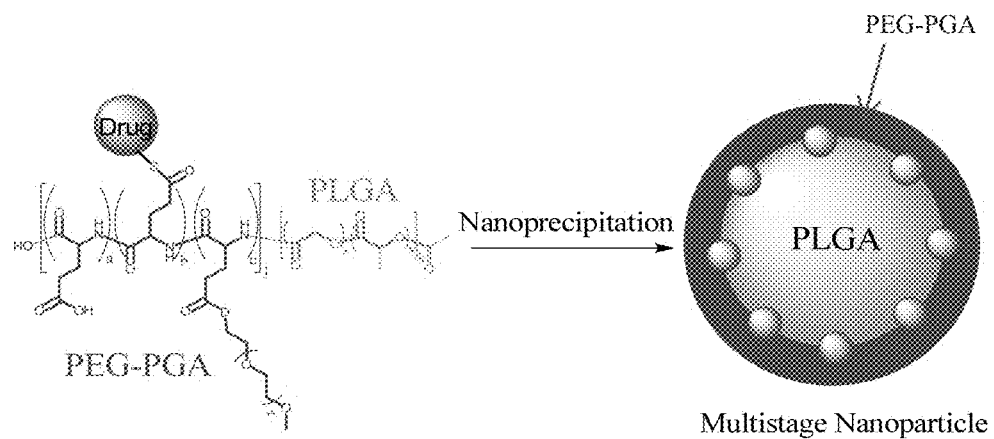
FIGS. 1A and 1B schematically illustrate multistage nanoparticles containing a hydrophobic core, formed from hydrophobic polymer segments, and a hydrophilic shell composed of small nanoparticles formed from hydrophilic polymer segments.

Nanoparticles for selective, two stage delivery to tumors have been developed. The nanoparticles are initially sized so that they preferentially accumulate in the tumor tissue as a result of leakage through the defective vasculature in the solid tumors. Once in the tumor tissue, the nanoparticles are cleaved hydrolytically and/or by enzymatic cleavage over time to release smaller nanoparticles carrying therapeutic, prophylactic and/or diagnostic agents into the necrotic interior of the tumors. This provides a simple, elegant, and highly selective means of delivering one or more drugs selectively, not just to tumors generally, but, more importantly, into the poorly vascularized necrotic interiors where drugs are normally unable to penetrate. The nanoparticles have a number of advantages, including: less toxicity due to selective accumulation only in the tumors; access into the poorly vascularized necrotic interiors of the tumor; and/or sustained release over a period of time within the tumor.

I. Definitions

"Drug", as used herein, refers to a physiologically or pharmacologically active agent that acts locally and/or systemically in the body. Drugs are substances that are administered to a subject for the treatment (e.g., therapeutic agent), prevention (e.g., prophylactic agent), and/or diagnosis (e.g., diagnostic agent) of a disease or disorder.

"Anti-neoplastic agent", as used herein, refers to a drug that either inhibits the growth and multiplication of neoplastic cells, such as by interfering with the cell's ability to replicate DNA, and/or is cytotoxic to neoplastic cells.

"Effective amount" or "therapeutically effective amount", as used herein, refers to an amount of polymer-drug conjugate effective to decrease the size of a solid tumor or to inhibit the growth of a solid tumor.

"Biocompatible" and "biologically compatible", as used herein, generally refer to materials that are, along with any metabolites or degradation products thereof, generally nontoxic to the recipient, and do not cause any significant adverse effects to the recipient. Generally speaking, biocompatible materials are materials which do not elicit a significant inflammatory or immune response when administered to a patient.

"Biodegradable polymer" and "bioerodible polymer" are used herein interchangeably, and generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment. Suitable degradation times are from hours to weeks, more preferable from hours to days. For example, the polymer may degrade over a time period from one hour to fourteen days, from three hours to seven days, from twelve hours to seven days, or from eighteen hours to two days.

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Hydrophilic", as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic", as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

"Solid Tumor", as used herein, refers to an abnormal mass of tissue that results from the proliferation of cells. Typically, solid tumors do not contain cysts or liquid areas within the tissue mass. Solid tumors can arise in any part of the body, and may be benign (not cancerous) or malignant (cancerous). Most types of cancer other than leukemias can form solid tumors. Solid tumors include, for example, adenocarcinomas, carcinomas, hemangiomas, liposarcomas, lymphomas, melanomas and sarcomas. The term can also be used to refer to conditions such as endometriosis, caused by uncontrolled proliferation of cells, to the extent these tissues are characterized by leaky vasculature.

"Small Molecule", as used herein, refers to a molecule, such as an organic or organometallic compound, with a molecular weight of less than 2,000 Daltons, less than 1,500 Daltons, less than 1,000 Daltons, less than 750 Daltons, or less than 500 Daltons. The small molecule can be a hydrophilic, hydrophobic, or amphiphilic compound.

"Nanoparticle", as used herein, generally refers to a particle of any shape having a diameter from about 1 nm up to, but not including, about 1 micron, preferably from 3 nm to about 200 nm. Nanoparticles having a spherical shape are generally referred to as "nanospheres". The size of nanoparticles can be experimentally determined using a variety of methods known in the art, including transmission electron microscopy (TEM), dynamic light scattering (DLS), gel filtration chromatography (GFC), and fluorescence correlation spectroscopy (FCS).

"Multistage nanoparticles", as used herein, refers to nanoparticles which release one or more smaller nanoparticles as a result of cleavage or degradation of the nanoparticles, such as hydrolytic or enzymatic cleavage of the nanoparticle.

"Mean particle size" or "average particle size", as used herein, generally refers to the statistical mean particle size (diameter) of the nanoparticles in a population of nanoparticles. The diameter of an essentially spherical nanoparticle may refer to the physical or hydrodynamic diameter. The diameter of a non-spherical nanoparticle may refer preferentially to the hydrodynamic diameter. As used herein, the diameter of a non-spherical nanoparticle may refer to the largest linear distance between two points on the surface of the nanoparticle. Mean particle size can be measured using methods known in the art, such as dynamic light scattering.

"Monodisperse" and "homogeneous size distribution" are used interchangeably herein and describe a population of nanoparticles where all of the nanoparticles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Spacer" or "Spacer Group", as used herein, refers to a group or moiety which is at minimum bivalent, and connects one or more drugs to the hydrophilic polymer segment. Spacers can be composed of any assembly of atoms, including oligomeric and polymeric chains.

"Linker" or "Linker Group", as used herein, refers to a bivalent group or moiety which connects the hydrophilic polymer segment and the hydrophobic polymer segment. Preferably, the linker is designed to be cleaved in response to an endogenous stimulus characteristic of the tumor microenvironment, such as a change in pH or the presence of an enzyme.

II. Polymer-Drug Conjugates

The polymer-drug conjugates used forming nanoparticles for the multistage delivery of therapeutic agents to solid tumors contain hydrophobic polymer segment and a hydrophilic polymer segment. One or more drugs are covalently attached to the hydrophilic polymeric segment.

The nanoparticles are formed from one or more polymer-drug conjugates. In some instances, the polymer-drug conjugate is defined by Formula I $$(A-S)_b-X-L-Y \quad \text{Formula I}$$

wherein
  A is, independently for each occurrence, a drug;
  S is absent, or is a spacer group;
  X is a hydrophilic polymer segment;
  L is absent, or is a linking group;
  Y is a hydrophobic polymer segment; and
  b is an integer between 1 and 100.

In some embodiments of Formula I, A is a small molecule anti-neoplastic agent. The one or more drugs can optionally be connected to the hydrophilic polymer segment by means of a spacer. The spacer can include any number of atoms; however, the total number of atoms in the spacer group is preferably between 3 and 200 atoms, more preferably between 3 and 150 atoms, more preferably between 3 and 100 atoms, most preferably between 3 and 50 atoms. In some embodiments, the spacer is hydrophilic.

In some embodiments, the spacer is an alkyl group, an alkylaryl group, an oligo- or polyethylene glycol chain, or an oligo- or poly(amino acid) chain. The spacer can includes one or more heteroatoms, one or more cleavable subunits, such as a oligo- or poly(peptide) that can be enzymatically cleaved, and/or one or more hydrolysable functional groups, such as an ester or amide, or combinations thereof.

The hydrophilic polymer segment can be any biocompatible hydrophilic homopolymer or copolymer. In some embodiments, the hydrophilic polymer segment is a graft copolymer containing a polymeric backbone functionalized by one or more hydrophilic polymeric side chains. In particular embodiments, the hydrophilic polymer segment is a graft copolymer composed of a poly-glutamic acid backbone functionalized by one or more poly(ethylene glycol) (PEG) side chains. In some embodiments, the poly-glutamic acid backbone is poly-L-glutamic acid.

The hydrophobic polymer segment can be any biocompatible hydrophobic polymer or copolymer. In some embodiments, the hydrophobic polymer segment is a biodegradable aliphatic polyester. In particular embodiments, the hydrophobic polymer segment is poly(lactic acid), poly(glycolic acid), or poly(lactic acid-co-glycolic acid).

In some embodiments, the polymer-drug conjugate is defined by Formula II x and y are each, independently, an integer between 1 and 1000, more preferably between 1 and 500, most preferably between 1 and 100;

z is, independently for each occurrence, an integer between 1 and 1000, more preferably between 1 and 500, most preferably between 1 and 100; and j and k are each, independently, an integer between 1 and 1000, more preferably between 1 and 500.

In some embodiments of Formula II, A is a small molecule anti-neoplastic agent. In particular embodiments, A is an anthracycline, such as doxorubicin or daunorubicin, or a topoisomerase inhibitor, such as camptothecin.

In some embodiments of Formula II, S is absent. In other embodiments, S is a defined above.

In some embodiments of Formula II, D is, independently for each occurrence, O or NH. In some embodiments, D is, in every occurrence, O. In still other embodiments, D is, in every occurrence, NH.

In some embodiments of Formula II, L is absent. In other embodiments, L is a cleavable linker which is designed to be cleaved in response to an endogenous stimulus characteristic of the tumor microenvironment, such as a change in pH or the presence of an enzyme. The linker may include one or more hydrolysable functional groups, such as an ester, amide, or glycosidic bond, which can be hydrolyzed in acidic conditions. The linker can include an oligo- or poly(peptide) sequence designed to be cleaved by a matrix metalloproteinases (MMPs), such as matrix metalloproteinase-2 (MMP-2) or matrix metalloproteinase-9 (MMP-9).

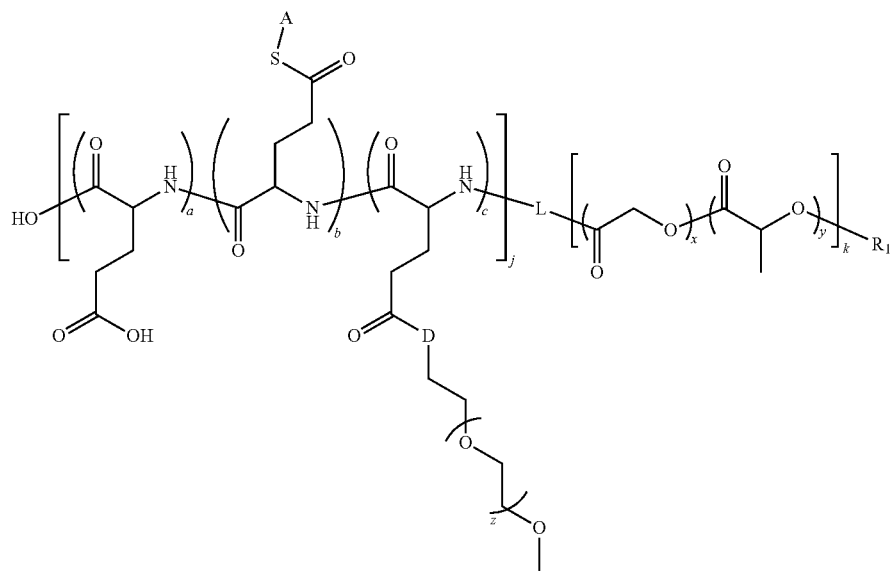

Formula II wherein
A is a drug;
S is absent, or is a spacer group;
L is absent, or is a linking group;
D is, independently for each occurrence, O, S, or $NR_1$;
$R_1$ is H or a $C_1$-$C_{12}$ alkyl group optionally containing between one and six oxygen heteroatoms;
a, b, c, and d are each, independently, an integer between 1 and 1000, more preferably between 1 and 500, most preferably between 1 and 100;

The linker also includes an oligo- or poly(peptide) sequence designed to be cleaved by a cathepsin, such as Cathepsin B. The linker can include an oligo- or poly(peptide) sequence designed to be cleaved by autotaxin.

In other embodiments, the hydrophobic polymer segment, along with an optional linking group, is grafted onto the backbone of the hydrophilic polymer segment. In one embodiment, the polymer-drug conjugate is defined by Formula III.

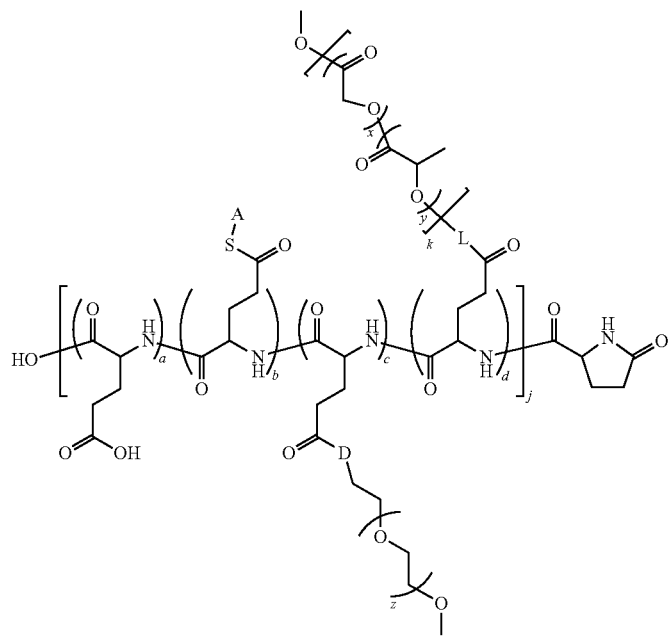

Formula III wherein
A is a drug;
S is absent, or is a spacer group;
L is absent, or is a linking group;
D is, independently for each occurrence, O, S, or $NR_1$;
$R_1$ is H or a $C_1$-$C_{12}$ alkyl group optionally containing between one and six oxygen heteroatoms;
a, b, c, and d are each, independently, an integer between 1 and 1000, more preferably between 1 and 500, most preferably between 1 and 100;
x and y are each, independently, an integer between 1 and 1000, more preferably between 1 and 500, most preferably between 1 and 100;
z is, independently for each occurrence, an integer between 1 and 1000, more preferably between 1 and 500, most preferably between 1 and 100; and
j and k are each, independently, an integer between 1 and 1000, more preferably between 1 and 500.

In some embodiments of Formula III, A is a small molecule anti-neoplastic agent. In particular embodiments, A is an anthracycline, such as doxorubicin or daunorubicin, or a topoisomerase inhibitor, such as camptothecin.

In some embodiments of Formula III, S is absent. In other embodiments, S is a defined above.

In some embodiments of Formula III, D is, independently for each occurrence, O or NH. In some embodiments, D is, in every occurrence, O. In still other embodiments, D is, in every occurrence, NH.

In some embodiments of Formula III, L is absent. In other embodiments, L is a cleavable linker which is designed to be cleaved in response to an endogenous stimulus characteristic of the tumor microenvironment, such as a change in pH or the presence of an enzyme. The linker may include one or more hydrolysable functional groups, such as an ester, amide, or glycosidic bond, which can be hydrolyzed in acidic conditions. The linker can include an oligo- or poly (peptide) sequence designed to be cleaved by a matrix metalloproteinases (MMPs), such as matrix metalloproteinase-2 (MMP-2) or matrix metalloproteinase-9 (MMP-9).

The linker also includes an oligo- or poly(peptide) sequence designed to be cleaved by a cathepsin, such as Cathepsin B. The linker can include an oligo- or poly(peptide) sequence designed to be cleaved by autotaxin.

In other embodiments, the polymer is by Formula IV

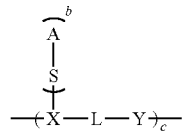

Formula IV wherein
A is, independently for each occurrence, a drug;
S is absent, or is a spacer group;
X is a hydrophilic polymer segment;
L is absent, or is a linking group;
Y is a poly(alkylene oxide) or copolymer thereof; and
b and c are, independently, integers between 1 and 100.

In some embodiments of Formula IV, A is a small molecule anti-neoplastic agent. The one or more drugs can optionally be connected to the hydrophilic polymer segment by means of a spacer, as defined above. In some embodiments, the spacer is an alkyl group, an alkylaryl group, an oligo- or polyethylene glycol chain, or an oligo- or poly (amino acid) chain. The spacer can include one or more heteroatoms, one or more cleavable subunits, such as a oligo- or poly(peptide) that can be enzymatically cleaved, and/or one or more hydrolysable functional groups, such as an ester or amide.

The hydrophilic polymer segment can be any biocompatible hydrophilic homopolymer or copolymer. In some embodiments, the hydrophilic polymer segment is a graft copolymer containing a polymeric backbone functionalized by one or more hydrophilic polymeric side chains. In particular embodiments, the hydrophilic polymer segment is a graft copolymer composed of a poly-glutamic acid backbone functionalized by one or more poly(ethylene glycol) (PEG) side chains. In some embodiments, the poly-glutamic acid backbone is poly-L-glutamic acid.

Y can be any suitable poly(alkylene oxide) or copolymer thereof. In certain embodiments, Y is PEG, or a copolymer thereof.

In some embodiments, the polymer-drug conjugate is defined by Formula V $R_1$ is H or a $C_1$-$C_{12}$ alkyl group optionally containing between one and six oxygen heteroatoms;

a, b, c, and d are each, independently, an integer between 1 and 1000, more preferably between 1 and 500, most preferably between 1 and 100;

z is, independently for each occurrence, an integer between 1 and 1000, more preferably between 1 and 500, most preferably between 1 and 100; and

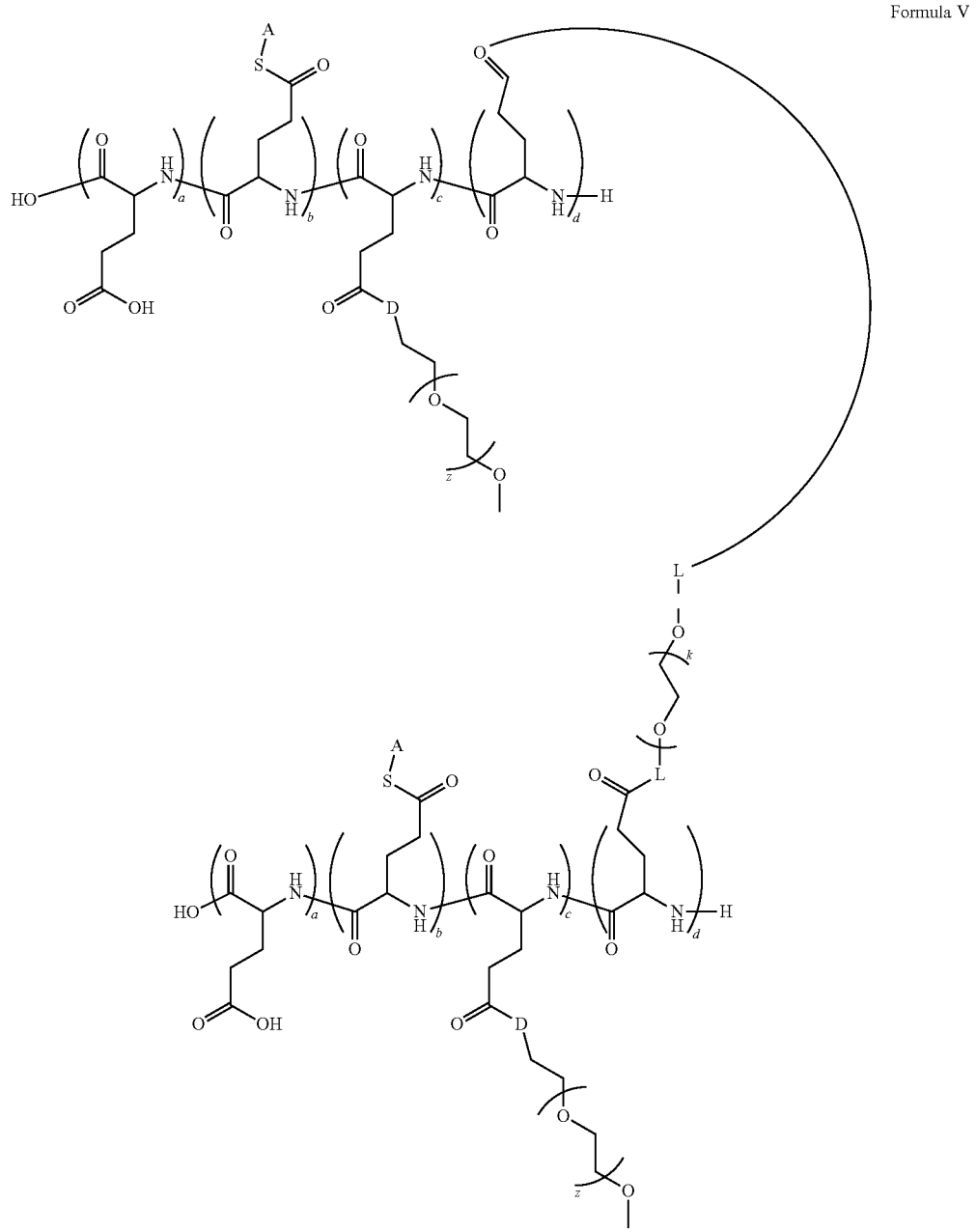

Formula V wherein
A is a drug;
S is absent, or is a spacer group;
L is absent, or is a linking group;
D is, independently for each occurrence, O, S, or $NR_1$;

k is an integer between 1 and 1000, more preferably between 1 and 500.

In some embodiments of Formula V, A is a small molecule anti-neoplastic agent. In particular embodiments, A is an anthracycline, such as doxorubicin or daunorubicin, or a topoisomerase inhibitor, such as camptothecin.

In some embodiments of Formula V, S is absent. In other embodiments, the spacer is as defined above.

In some embodiments of Formula V, D is, independently for each occurrence, O or NH. In some embodiments, D is, in every occurrence, O. In still other embodiments, D is, in every occurrence, NH.

In some embodiments of Formula V, L is absent. In other embodiments, L is a cleavable linker which is designed to be cleaved in response to an endogenous stimulus characteristic of the tumor microenvironment, such as a change in pH or the presence of an enzyme. The linker may include one or more hydrolysable functional groups, such as an ester, amide, or glycosidic bond, which can be hydrolyzed in acidic conditions. The linker can include an oligo- or poly(peptide) sequence designed to be cleaved by a matrix metalloproteinases (MMPs), such as matrix metalloproteinase-2 (MMP-2) or matrix metalloproteinase-9 (MMP-9). The linker also includes an oligo- or poly(peptide) sequence designed to be cleaved by a cathepsin, such as Cathepsin B. The linker can include an oligo- or poly(peptide) sequence designed to be cleaved by autotaxin.

In particular embodiments, the hydrophilic polymer segment is a graft copolymer composed of a poly-glutamic acid backbone functionalized by one or more poly(ethylene glycol) (PEG) side chains. In some embodiments, the polyglutamic acid backbone is poly-L-glutamic acid. In some of these embodiments, the molecular weight of the polyglutamic acid polymer is typically greater than about 5000 Daltons, preferably between about 2 kDa to about 80 kDa, more preferably from about 5 kDa to about 60 kDa, and most preferably from about 9 kDa to about 50 kDa, as determined by viscosity.

In some of these embodiments, the percent loading of the drug by weight on the hydrophilic polymer segment, with or without the linking group, preferably ranges from about 7% to about 50% by weight, more preferably from about 10% to about 35% by weight, and most preferably from about 15% to about 30% by weight. In some instances, the percent loading of the PEG on the hydrophilic polymer segment is preferably ranges from about 1% to about 75%, more preferably from about 5% to about 70%, and most preferably from about 10% to about 65%.

In some embodiments, the polymer-drug conjugate is one of the following:

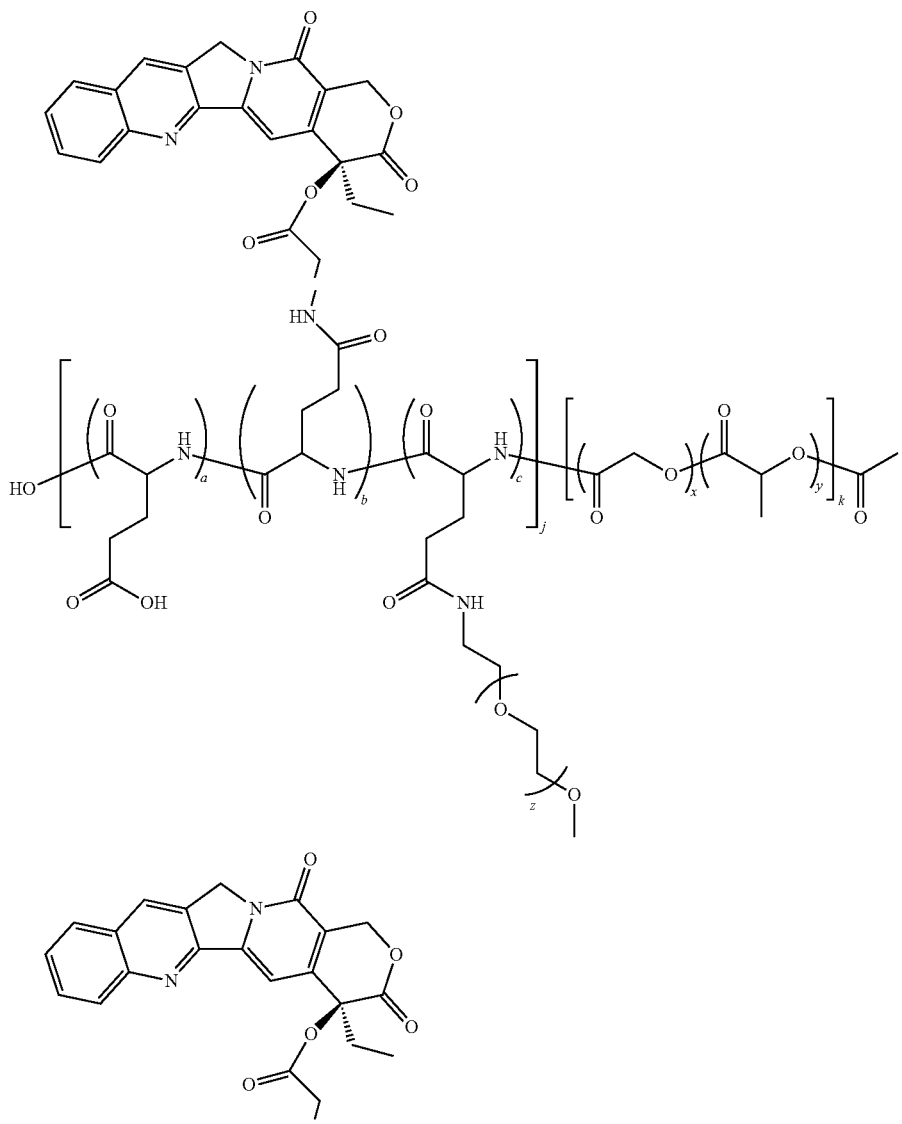

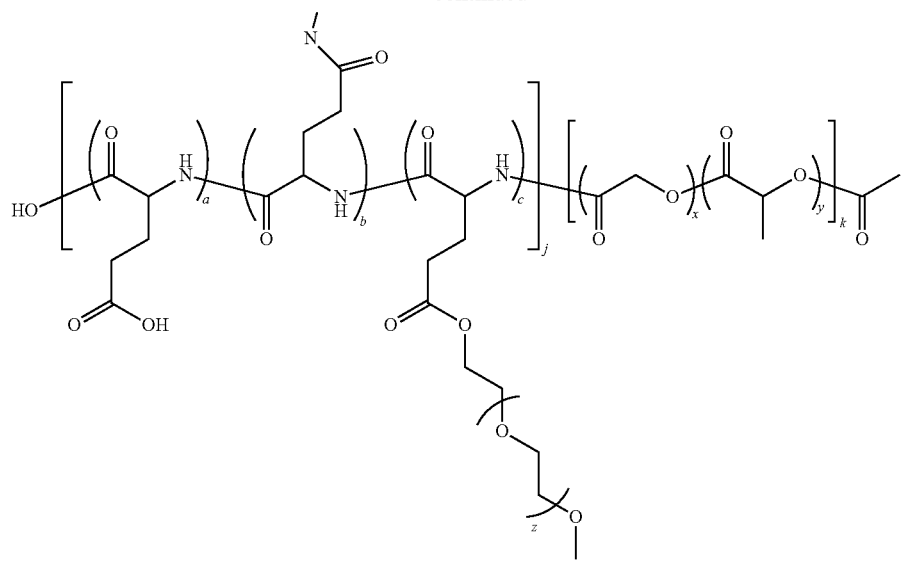
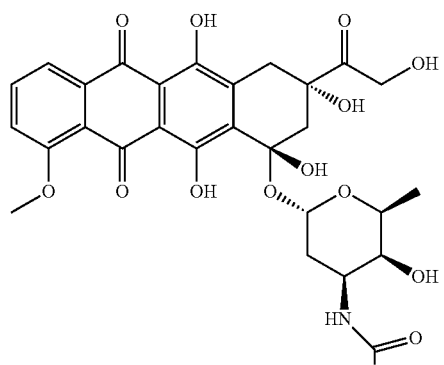
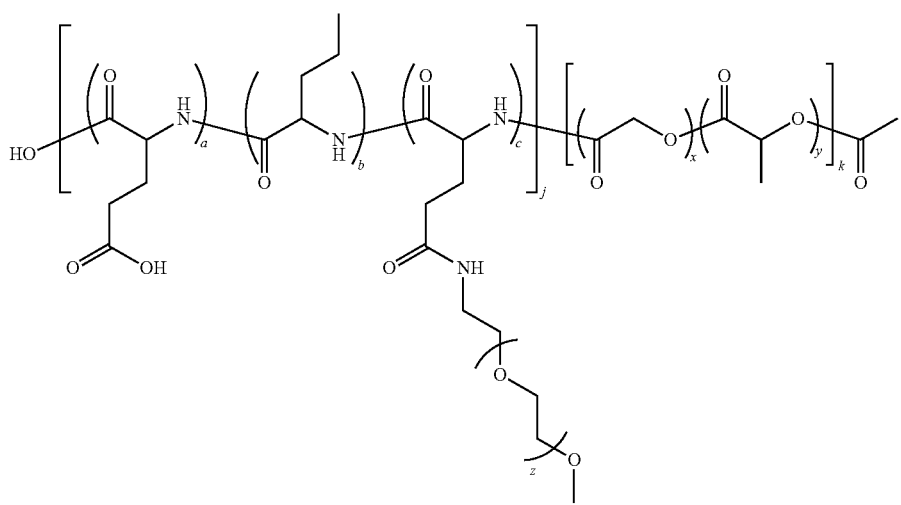

-continued

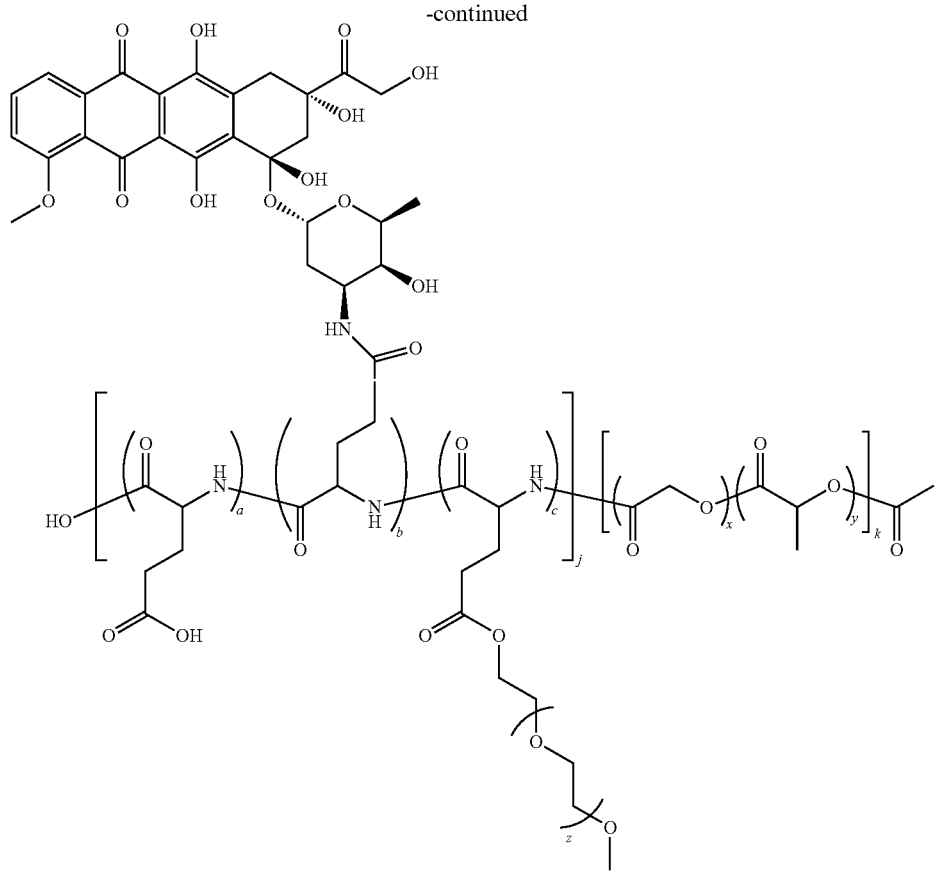

a, b, and c are each, independently, an integer between 1 and 1000, more preferably between 1 and 500, most preferably between 1 and 100;

x and y are each, independently, an integer between 1 and 1000, more preferably between 1 and 500, most preferably between 1 and 100;

z is, independently for each occurrence, an integer between 1 and 1000, more preferably between 1 and 500, most preferably between 1 and 100; and j and k are each, independently, an integer between 1 and 1000, more preferably between 1 and 500.

A. Therapeutic, Prophylactic and Diagnostic Agents

The polymer-drug conjugate contains one or more therapeutic, prophylactic and/or diagnostic drug molecules covalently attached to the hydrophilic polymer segment. Generally, the one or more drug molecules are covalently attached to a sidechain of the hydrophilic polymer segment. Drug molecules can also be covalently attached to an endgroup of the hydrophilic polymer segment.

The number of drug molecules bound to the hydrophilic polymer segment of the polymer drug conjugate can be varied in view of a range of factors, including the identity of the one or more anti-neoplastic agents, the tumor to be treated, and the overall design of the therapeutic regimen. In some embodiments, the polymer-drug conjugate contains only a single drug bound to the hydrophilic polymer segment. In other embodiments, more than one drug is bound to the hydrophilic polymer segment. In cases where multiple drugs are bound to the hydrophilic polymer segment, the drugs may be the same or different.

In some embodiments, one or more small molecule anti-neoplastic agents are covalently attached to the hydrophilic polymer segment. Representative anti-neoplastic agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and docetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as camptothecin, irinotecan, and topotecan as well as derivatives of epipodophyllotoxins such as amsacrine, etoposide, etoposide phosphate, and teniposide). In some embodiments, one or more topoisomerase inhibitors, such as camptothecin, are covalently attached to the hydrophilic polymer segment. In some embodiments, one or more anthracyclines, such as doxorubicin or daunorubicin, are covalently attached to the hydrophilic polymer segment.

One or more drugs can also be covalently attached to the hydrophobic polymer segment.

One or more diagnostic agents can also be attached to the polymer-drug conjugate, in addition to, or alternative to, the therapeutic or prophylactive agent. In these embodiments, the diagnostic agent is selected to, for example, enhance imaging of the solid tumor. Exemplary diagnostic agents include paramagnetic molecules, fluorescent compounds, magnetic molecules, and radionuclides, x-ray imaging agents, and contrast agents.

In some embodiments, one or more topoisomerase inhibitors, such as camptothecin, and/or one or more anthracyclines, such as doxorubicin or daunorubicin, are covalently attached to the hydrophilic polymer segment.

B. Hydrophilic Polymers

The hydrophilic polymer segment can be any hydrophilic biocompatible homopolymer or copolymer. Examples of suitable hydrophilic polymers include, but are not limited to, hydrophilic polypeptides, poly(amino acids) such as poly-L-glutamic acid (PGS), gamma-polyglutamic acid, poly-L-aspartic acid, poly-L-serine, or poly-L-lysine, poly(alkylene glycols) such as polyethylene glycol (PEG), poly(propylene glycol) (PPG), and copolymers of ethylene glycol and propylene glycol, poly(oxyethylated polyol), poly(olefinic alcohol), polyvinylpyrrolidone), poly(hydroxyalkylmethacrylamide), poly(hydroxyalkylmethacrylate), poly(saccharides), poly(hydroxy acids), poly(vinyl alcohol), as well as copolymers thereof.

In some embodiments, the hydrophilic polymer segment is a biocompatible block copolymer. In other embodiments, the hydrophilic polymer segment is a graft copolymer. Graft copolymers are branched copolymers containing a polymeric backbone functionalized by one or more hydrophilic polymeric side chains, in which the side chains are structurally distinct from the polymeric backbone. In these embodiments, both the polymeric backbone and the polymeric side chains may individually be homopolymers or copolymers. Furthermore, the one or more polymeric sidechains may have the same or different polymeric composition.

In certain embodiments, the hydrophilic polymer segment is a graft copolymer containing a poly(amino acid) polymer backbone, a carbohydrate polymer backbone, or combinations thereof. In some embodiments, the hydrophilic polymer segment is a graft copolymer composed of a polymeric backbone functionalized by one or more poly(alkylene glycol) side chains. The poly(alkylene glycol) chains may contain between 8 and 1000 repeat units, more preferably between 30 and 250 repeat units. Suitable poly(alkylene glycols) include polyethylene glycol, polypropylene 1,2-glycol, polypropylene oxide), polypropylene 1,3-glycol, and copolymers thereof. In certain embodiments, the one or more poly(alkylene glycol) side chains are PEG chains. In such cases, the PEG chains can be linear or branched, such as those described in U.S. Pat. No. 5,932,462. Preferably, the PEG chains are linear. Suitable poly(alkylene glycol) side chains also include block copolymers containing one or more poly(alkylene glycol) segments, such as a poloxamer.

In certain embodiments, the PEG chains have an average molecular weight of between 1,000 and 10,000 Daltons.

The density of grafted polymeric sidechains on the polymeric backbone of the hydrophilic polymer segment will influence the surface chemistry of the nanoparticles ultimately formed from the polymer-drug conjugate. Preferably, the grafting ratio of the graft copolymer is sufficiently high to provide nanoparticles that exhibit or present significant amounts of a hydrophilic biocompatible polymer, such as PEG, on their surface to ensure biocompatibility and enhance circulation time.

As described below, the hydrophilic polymer segment will form small nanoparticles upon release from the larger nanoparticles. The density of grafted polymeric sidechains on the polymeric backbone of the hydrophilic polymer segment will therefore also influence the surface chemistry of the resulting small nanoparticles. In general, a high grafting ratio, for example, a large number of PEG sidechains attached to the polymeric backbone of the graft copolymer, enhances the diffusion of the small nanoparticles through the interstitial matrix of the solid tumor. However, a high PEG grafting ratio can also reduce uptake of the small nanoparticles into the tumor cells. Therefore, in some embodiments, the grafting ratio is selected to provide small nanoparticles that both readily diffuse through the interstitial matrix of the solid tumor and are readily taken up by tumor cells.

In certain instances, the grafting ratio ranges between about 1.5% and about 60%, more preferably between about 3% and about 30%.

The grafted polymeric sidechains may be covalently attached to the polymeric backbone via any suitable moiety. Generally, PEG chains are covalently attached to the polymeric backbone via a hydrolysable functional group, such as an amide, ester, or thioester. The hydrolysable functional group can also be selected to vary the rate of side chain hydrolysis. For example, the hydrolysable functional group can be the same or different for each grafted PEG chain in the graft copolymer. As a result, the hydrolysis rate of the side chains can be varied over time. As the PEG chains are hydrolytically cleaved over time, the diffusion rate of the particles will decrease while their rate of uptake by tumor cells will increase. In some embodiments, all of the grafted PEG chains are covalently attached via amide bonds. In other embodiments, all of the grafted PEG chains are covalently attached via ester bonds. In still other embodiments, some of the grafted PEG chains are covalently attached via ester bonds and some of the grafted PEG chains are covalently attached by amide bonds.

In embodiments where the hydrophilic polymer segment is a graft copolymer, the polymeric backbone of the graft copolymer may be hydrophobic or hydrophilic; however, preferably it is hydrophilic. In some embodiments, the polymeric backbone of the graft copolymer is a poly(amino acid), such as poly-L-glutamic acid or gamma-poly(glutamic acid) (PGA).

In some embodiments, the hydrophilic polymer segment is a graft copolymer containing a poly-glutamic acid backbone functionalized by one or more PEG side chains. In some embodiments, the poly-glutamic acid backbone is poly-L-glutamic acid.

C. Spacer Between Drug and Hydrophilic Polymer

Polymer-drug conjugates can optionally contain a spacer that connects one or more drugs to the hydrophilic polymer segment. The spacer must be at minimum bivalent; however, in some embodiments, the spacer can be polyvalent, and connect multiple drugs to the hydrophobic polymer segment.

Spacers can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, most preferably between 3 and 50 atoms.

In some embodiments, the spacer is an alkyl group, an alkylaryl group, an oligo- or polyethylene glycol chain, or an oligo- or poly(amino acid) chain. the spacer is hydrophilic. The spacer may also include one or more heteroatoms, one or more cleavable subunits, such as a oligo- or poly(peptide) that can be enzymatically cleaved, one or more hydrolysable functional groups, such as an ester or amide, as well as combinations thereof.

In many cases, the spacer is a linear moiety; however, in some embodiments, the spacer contains one or more branch points. Branched spacers can be used to attach multiple drugs to the hydrophilic polymer segment. In some embodiments, the spacer contains one or more branch points, and the terminus of each branch is connected to a drug. In one such embodiment, a dendritic spacer is used, with the hydrophilic polymer segment bound to the focal point of the dendrimer, and multiple drugs bound to the ends of the dendritic branches.

Representative spacers include an alkyl group, an alkylaryl group, an oligo- or polyethylene glycol chain, or an oligo- or poly(amino acid) chain. the spacer includes one or more heteroatoms, one or more cleavable subunits, such as a oligo- or poly(peptide) that can be enzymatically cleaved, one or more hydrolysable functional groups, such as an ester or amide.

D. Hydrophobic Polymer

The hydrophobic polymer segment can be any biocompatible hydrophobic polymer or copolymer. In some embodiments, the hydrophobic polymer segment is a biocompatible block copolymer.

The hydrophobic polymer segment can be biodegradable or non-biodegradable. In instances where the hydrophobic polymer segment is not biodegradable, a linker, preferably a cleavable linker, is present and connects the hydrophobic polymer segment to the hydrophilic polymer segment.

In some embodiments, the hydrophobic polymer segment is a biodegradable polymer. In cases where the hydrophobic polymer is biodegradable, the polymer degradation profile may be selected to influence the release rate of smaller nanoparticles in vivo. For example, the hydrophobic polymer segment can be selected to degrade over a time period from one hour to fourteen days, from three hours to seven days, from twelve hours to seven days, or from eighteen hours to two days.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof.

In certain embodiments, the hydrophobic polymer segment is an aliphatic polyester. In some embodiments, the hydrophobic polymer segment is poly(lactic acid), poly (glycolic acid), or poly(lactic acid-co-glycolic acid).

The molecular weight of the hydrophobic polymer segment can be varied to tailor the properties of nanoparticles formed from the polymer-drug conjugates. For example, the molecular weight of the hydrophobic polymer segment can be varied to engineer nanoparticles possessing the required average particle size and degradation profile. The hydrophobic polymer segment has a molecular weight of between about 150 Da and about 100 kDa, more preferably between about 1 kDa and about 75 kDa, most preferably between about 5 kDa and about 50 kDa.

E. Linkers

The polymer-drug conjugates can optionally contain a linker that connects the hydrophobic polymer segment and the hydrophilic polymer segment.

The linker may be cleavable. In some embodiments, the linker is designed to be cleaved in response to an endogenous stimulus characteristic of the tumor microenvironment, such as a change in pH or the presence of an enzyme. Linkers can contain any assembly of atoms, including oligomeric and polymeric chains. In some embodiments, the linker is an alkyl group, an alkylaryl group, an oligo- or polyethylene glycol chain, or an oligo- or poly(amino acid) chain.

The linker may include one or more hydrolysable functional groups designed to be hydrolyzed in the acidic environment of the tumor. For example, the linker can include one or more ester, amide, or glycosidic bonds that can be hydrolyzed in acidic conditions.

The linker may include one or more moieties that are designed to be enzymatically cleaved in the tumor microenvironment. Tumors are known to contain high concentrations of many proteases, including matrix metalloproteinases (MMPs), cathepsins, and autotaxins. In particular, levels of matrix metalloproteinase-2 (MMP-2) and matrix metalloproteinase-9 (MMP-9) are known to be high in regions where the nanoparticles are likely to extravasate, including the invasive edge of tumors and at the sites of angiogenesis.

For example, the linker may include an oligo- or poly (peptide) sequence designed to be cleaved by an MMP or a cathepsin, such as Cathepsin B. In some embodiments, the linker includes an oligo- or poly(peptide) sequence designed to be cleaved by a MMP-2 and/or MMP-9, such as PLGLAG (SEQ. ID. NO.: 1) or PLGVRG (SEQ. ID. NO.: 2). In some embodiments, the linker includes an oligo- or poly(peptide) sequence designed to be cleaved by a cathepsin B, such as an oligo- or poly(peptide) sequence containing multiple consecutive arginine residues. The linker can include an oligo- or poly(peptide) sequence designed to be cleaved by autotaxin.

III. Synthesis of Polymer-Drug Conjugates and Nanoparticles

A. Synthesis of Polymer-Drug Conjugates

Polymer-drug conjugates can be prepared using synthetic methods known in the art. Representative methodologies for the preparation of polymer-drug conjugates are discussed below. The appropriate route for synthesis of a given polymer-drug conjugate can be determined in view of a number of factors, such as the structure of the polymer-drug conjugate, the composition of the polymer segments which make up the polymer-drug conjugate, the identity of the one or more drugs attached to the polymer-drug conjugate, as well as the structure of the conjugate and its components as it relates to compatibility of functional groups, protecting group strategies, and the presence of labile bonds.

In addition to the synthetic methodologies discussed below, alternative reactions and strategies useful for the preparation of the polymer-drug conjugates disclosed herein are known in the art. See, for example, March, "Advanced Organic Chemistry," $5^{th}$ Edition, 2001, Wiley-Interscience Publication, New York).

Generally, polymer-drug conjugates are prepared by first forming the polymeric components of the polymer-drug conjugate, and then covalently attaching one or more drugs to the conjugate.

For example, representative polymer-drug conjugate containing a poly(lactic acid-co-glycolic acid) hydrophobic polymer segment and a graft copolymer hydrophilic polymer segment composed of a poly-L-glutamic acid backbone functionalized by one or more poly(ethylene glycol) (PEG) side chains and one or more camptothecin molecules connected to the polymeric backbone by a glycine spacer (1, below), can be synthesized as described below.

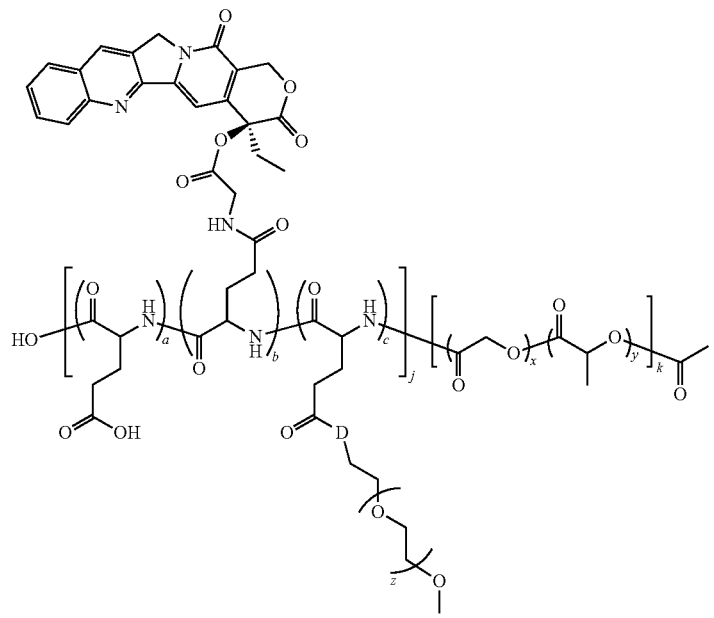

Preparation of 1 can begin with preparation of the hydrophilic polymer segment, as shown in Scheme 1. Formation of the hydrophilic segment can proceed from commercially-available N6-CBZ-L-lysine (2). Reaction of 2 with phosgene in THF, as described in International Publication No. WO2006/47703, affords compound 3. Reaction of compound 3 with mPEG-amine (4) under anhydrous conditions furnishes block copolymer 5. See, for example, Yokoyama, et al. *Bioconj. Chem.;* 3: 295-301 (1992). Subsequent deprotection of 5 with a base, such as sodium hydroxide, affords 6. See, for example, Yokoyama, et al. *Bioconj. Chem.;* 3: 295-301 (1992).

Scheme 1:

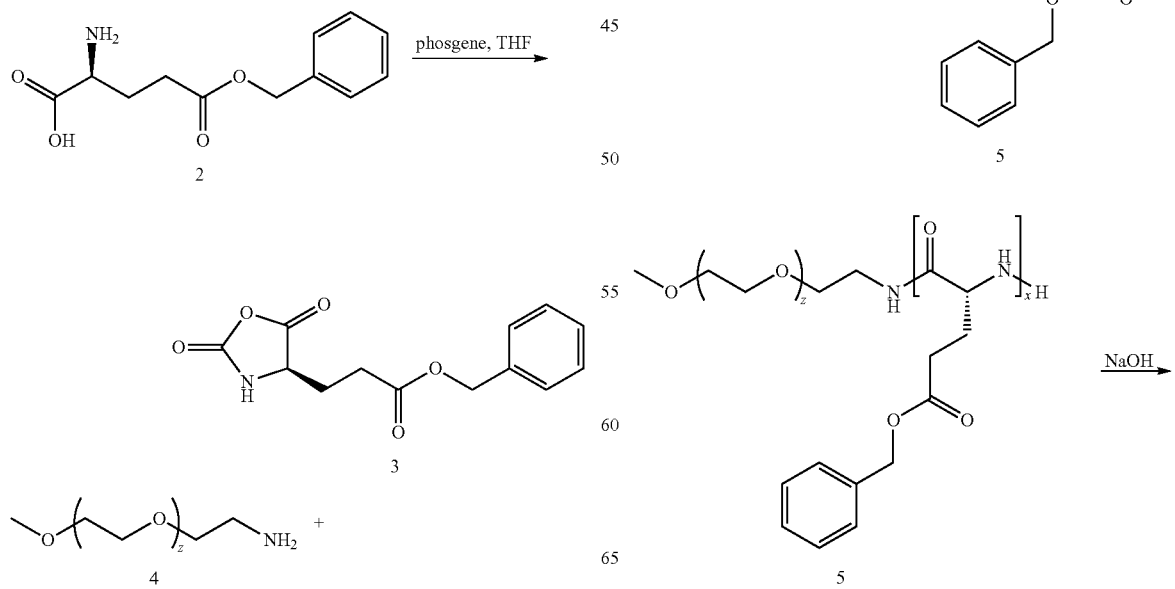

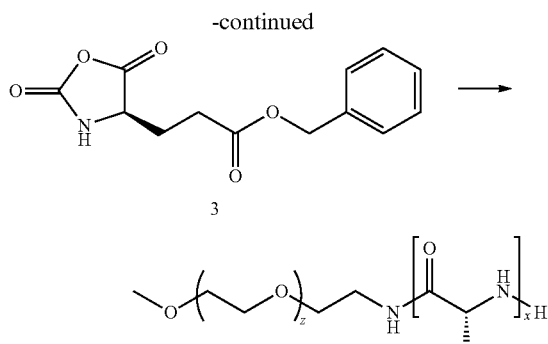

-continued

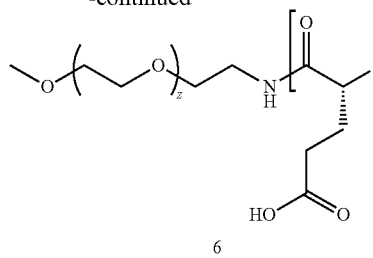
6

-continued

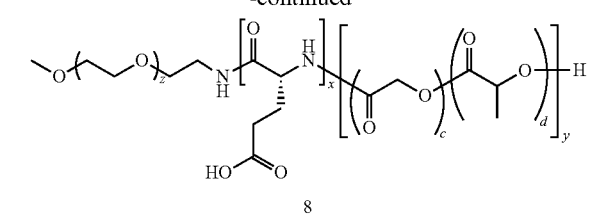
8

Next, the hydrophobic polymer segment can be covalently attached to the hydrophilic polymer segment, as shown in Scheme 2. Compound 6 can be reacted with N-hydroxysuccinimide-functionalized PLGA 7 under anhydrous conditions to furnish 8. See, for example, Chang, J., et al. *Biomaterials.*; 28: 869-876 (2007).

Synthesis of compound 1 can then be completed by covalently attaching the one or more hydrophilic polymer sidechains and the one or more active agents to the poly-L-glutamic acid backbone, as shown in Scheme 3. In the case of 1, one or more PEG chains and one or more camptothecin molecules are connected to the polymeric backbone. In the case of 1, the one or more camptothecin molecules are covalently attached to the polymer backbone by a glycine spacer.

8 can be reacted with glycine-functionalized campothecin (9) under standard amide bond-forming conditions (e.g., in the presence of a carbodiimide dehydrating agent, such as N,N'-dicyclohexylcarbodiimide (DCC), N,N'-Diisopropylcarbodiimide (DIC), or 1-Ethyl-3-(3-dimethylaminopropyl)carbodiimide (EDC) and a base, such as DMAP or triethylamine) to attach one or more camptothecin molecules to the polymeric backbone. Subsequently, the product of this reaction can be reacted with one or more mPEG-amine chains (10) under similar conditions to afford compound 1. These two reactions may be performed in any order, and optionally may be performed using a one-pot synthetic strategy. Alternatively, these two reactions may be performed simultaneously by reacting 8 with both 9 and 10 under standard amide bond-forming conditions.

Scheme 2:

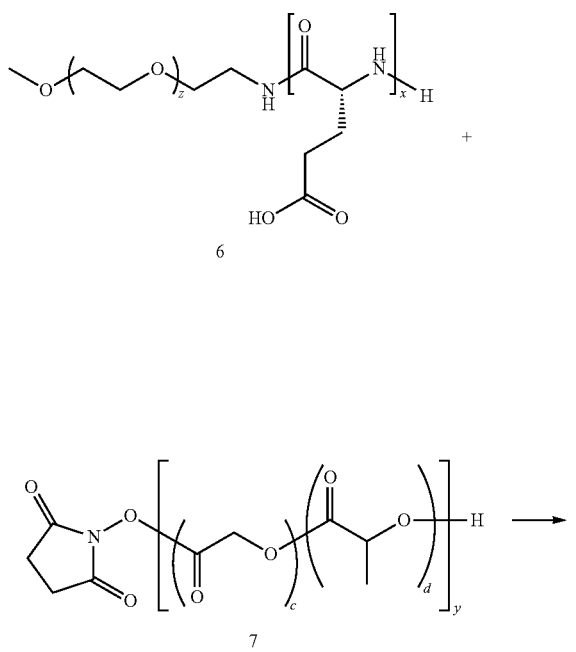

Scheme 3:

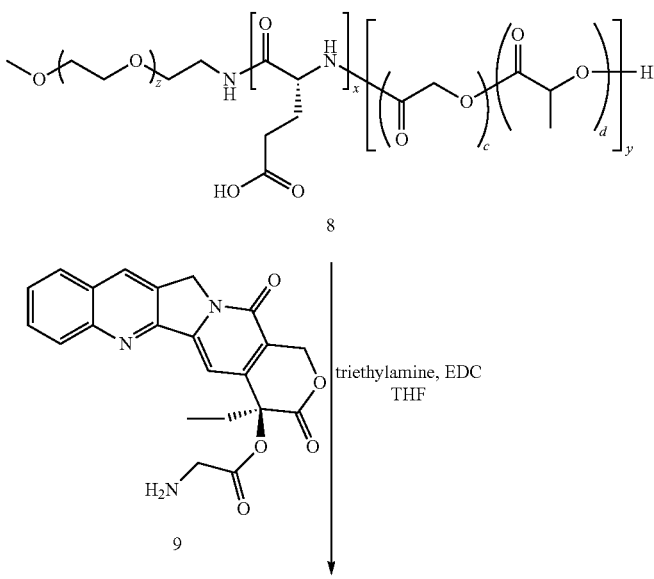

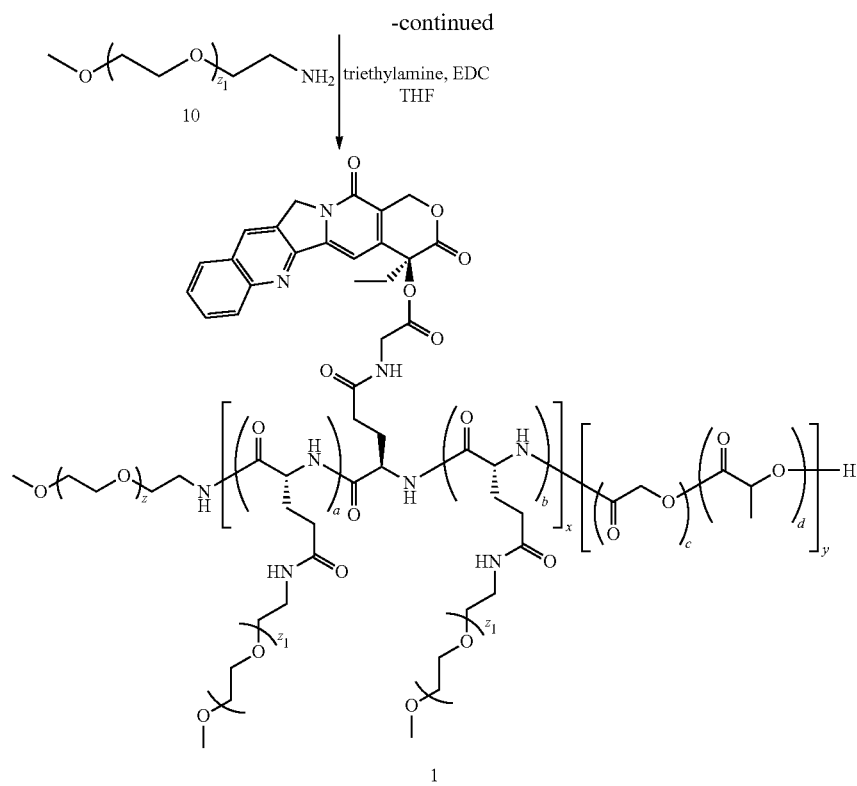

B. Polymer-Drug Conjugate Nanoparticles

Polymer-drug conjugates can be formed into nanoparticles using a variety of techniques known in the art. An appropriate method for particle formation can be selected in view of the physical and chemical properties of the one or more polymer-drug conjugates used to form the particles (i.e., stability and solubility) as well as the desired particle size and particle size distribution.

Nanoparticles can be formed from a single polymer-drug conjugate (i.e., the nanoparticles are formed from a polymer-drug conjugate which contains the same combination of drug, spacer, linker, hydrophobic polymer segment, and hydrophilic polymer segment). In other embodiments, the nanoparticles are formed from a mixture of one or more different polymer-drug conjugates. For example, nanoparticles may be formed from two or more polymer-drug conjugates containing different drugs and the same linker, spacer, hydrophobic polymer segment, and hydrophilic polymer segment or segments. Such nanoparticles can be used, for example, to co-administer two or more drugs.

In other cases, the nanoparticles are formed from two or more polymer-drug conjugates containing the same drug, and different linkers, spacers, hydrophobic polymer segments, and/or hydrophilic polymer segments. Such nanoparticles can be used, for example, to vary the release rate of drugs, the uptake rate of nanoparticles by tumor cells, and/or the diffusion rate of nanoparticles through tumor tissue. The nanoparticles can also be formed from two or more polymer-drug conjugates containing different drugs and different spacers, linkers, hydrophobic polymer segments, and/or hydrophilic polymer segments.

Nanoparticle Morphology

Figure 1B:
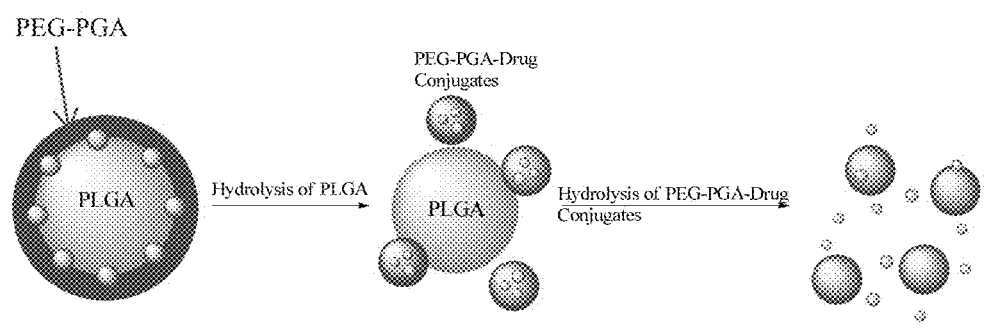
Figure 2A:
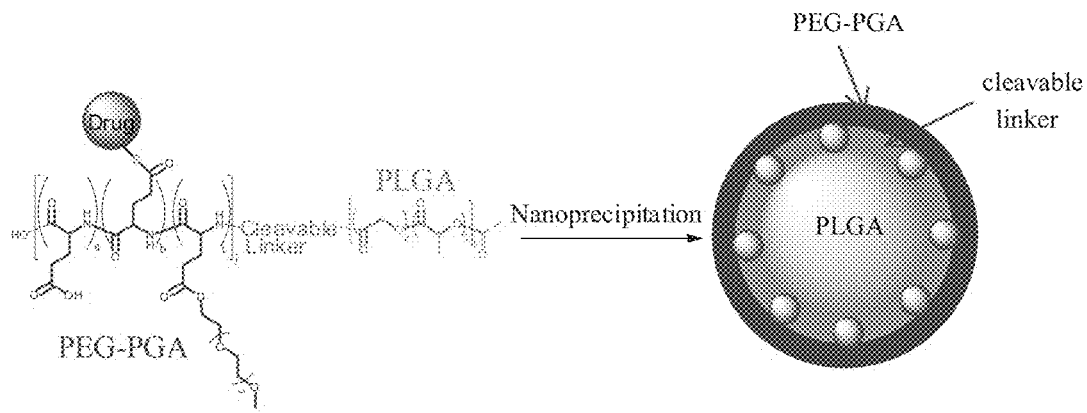
FIGS. 2A and 2B schematically illustrate multistage nanoparticles containing a hydrophobic core, formed from hydrophobic polymer segments, and a hydrophilic shell composed of small nanoparticles formed from the hydrophilic polymer segments which are connected by an enzymatically cleavable linking group.
Figure 2B:
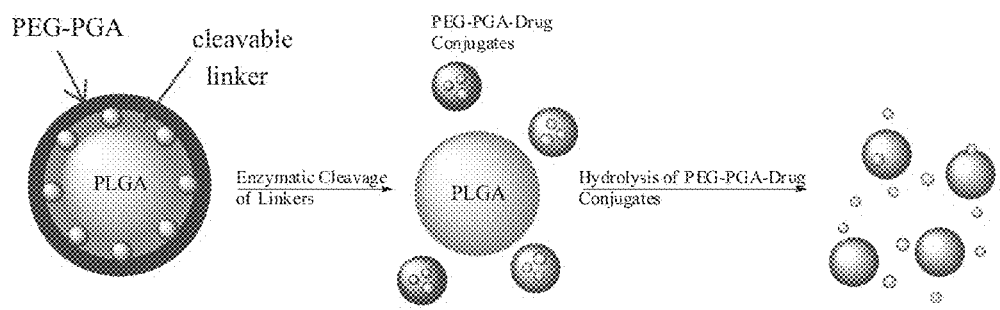

Nanoparticles formed from one or more polymer-drug conjugates may contain a hydrophobic core, formed from hydrophobic polymer segments, and a hydrophilic shell composed of small nanoparticles formed from the hydrophilic polymer segments. Multistage nanoparticles of this type are schematically illustrated in FIG. 1A. As shown in FIG. 1B, hydrolysis of multistage nanoparticles releases a plurality of smaller nanoparticles which can penetrate the tumor interior. In other embodiments, the nanoparticles formed from one or more polymer-drug conjugates may contain a hydrophobic core, formed from hydrophobic polymer segments, and a hydrophilic shell composed of small nanoparticles formed from the hydrophilic polymer segments which are connected by an enzymatically cleavable linking group. Multistage nanoparticles of this type are schematically illustrated in FIG. 2A. As shown in FIG. 2B, hydrolysis of multistage nanoparticles releases a plurality of smaller nanoparticles which can penetrate the tumor interior.

Figure 3:
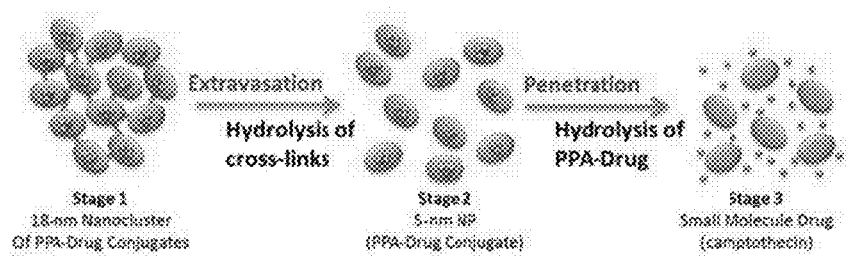
FIG. 3 schematically illustrates multistage nanoparticles formed from a plurality of small nanoparticles formed from hydrophilic polymer segments conjugated or joined together by poly(alkylene oxide) polymer or copolymer segments to form a larger nanoparticle or nanocluster. Once the nanoparticles have extravasated into the tumor tissue, the polymer segments joining the small nanoparticles are hydrolyzed, releasing a plurality of smaller nanoparticles, which can penetrate the tumor interior. A drug is released from these smaller nanoparticles within the tumor interior by hydrolysis.

In other cases, nanoparticles may contain a number of small nanoparticles formed from hydrophilic polymer segments conjugated or joined together by poly(alkylene oxide) polymer or copolymer segments to form a larger nanoparticle or nanocluster. Multistage nanoparticles of this type are schematically illustrated in FIG. 3.

In some embodiments, the nanoparticles exhibit significant amounts of a hydrophilic biocompatible polymer, such as PEG, on their surface. This surface chemistry imbues the nanoparticles with biocompatibility and ensures sufficient circulation time in vivo.

In embodiments where a linker covalently connects the hydrophobic polymer segments and the hydrophilic polymer segments, the nanoparticles will generally contain a hydrophobic core formed by the hydrophobic polymer segments, a shell formed by the linker groups, and a hydrophilic shell composed of small nanoparticles formed from the hydrophilic polymer segments.

The nanoparticles have an average particle size that causes the nanoparticles to preferentially accumulate within the perivascular tumor tissue via the EPR effect. The vasculature of tumors is typically characterized by blood vessels containing poorly-aligned defective endothelial cells with wide fenestrations (e.g., between 200-500 nm). As a result, nanoparticles with average particle sizes in this range, or slightly smaller, can preferentially extravasate out of the leaky regions of the tumor vasculature, and accumulate within the solid tumor. In some embodiments, the nanoparticles have an average particle size of between 8 nm and 500 nm, more preferably between 10 nm and 250 nm, most preferably between 12 nm and 200 nm.

In some embodiments, the population of nanoparticles is a monodisperse population of particles. In other embodiments, the population of nanoparticles is a polydisperse population of nanoparticles. In some instances where the population of nanoparticles is polydisperse, greater that 50% of the particle size distribution, more preferably 60% of the particle size distribution, most preferably 75% of the particle size distribution lies within 10% of the median particle size.

Once the nanoparticles have extravasated into the tumor tissue, the nanoparticles release one or more smaller nanoparticles. Preferably, the release of the one or more smaller nanoparticles is triggered by an endogenous stimulus characteristic of the tumor microenvironment, such as a change in pH or the presence of an enzyme.

As described above, the resulting small nanoparticles are generally formed from the hydrophilic polymer segments. The smaller nanoparticles possess an average particle size and surface chemistry which significantly lowers their diffusional hindrance in the interstitial matrix. In some embodiments, the smaller nanoparticles have an average particle size of between about 1 nm and about 20 nm, more preferably between about 2.5 nm and about 15 nm, most preferably between about 5 nm and about 10 nm. In some embodiments, the smaller nanoparticles exhibit significant amounts of a hydrophilic biocompatible polymer, such as PEG, on their surface which allows them to diffuse smoothly in the interstitial matrix, and reducing the binding, sequestration, and metabolism that hinders the transport of much smaller therapeutic agents.

Methods of Nanoparticle Formation

Nanoparticles formed from polymer-drug conjugates can be prepared using any suitable method for the formation of polymer nanoparticles known in the art. The method employed for nanoparticle formation will depend on a variety of factors, including the characteristics of the polymers present in the polymer-drug conjugate and the desired particle size and size distribution. The nature of the one or more drugs present in the particle-drug conjugate may also be a factor, as some agents are unstable in the presence of certain solvents, in certain temperature ranges, and/or in certain pH ranges.

Generally, a monodisperse population of nanoparticles is some for use in the methods described herein. In circumstances where a monodisperse population of nanoparticles is desired, the nanoparticles may be formed using a method which produces a monodisperse population of nanoparticles. Alternatively, methods producing polydisperse nanoparticle distributions can be used, and the nanoparticles can be separated following nanoparticle formation to provide a population of nanoparticles having the desired average particle size and particle size distribution. Such separations can be performed using methods known in the art, such as sieving.

Common techniques for preparing suitable polymeric nanoparticles include, but are not limited to, nanoprecipitation, solvent evaporation, hot melt particle formation, solvent removal, spray drying, phase inversion, and low temperature casting. In some embodiments, the nanoparticles are prepared using nanoprecipitation.

Pharmaceutically acceptable excipients, including pH modifying agents, disintegrants, preservatives, and antioxidants, can optionally be incorporated into the particles during particle formation.

1. Nanoparticles Formed by the Assembly of Polymer-Drug Conjugates with Hydrophobic Polymer Conjugates Nanoparticles can also be formed by assembling one or more polymer drug conjugates on the surface of a hydrophobic polymer nanoparticle. In some embodiments, one or more drugs, such as one or more anti-neoplastic agents, are dispersed in the hydrophobic polymer nanoparticle.

The hydrophobic polymer nanoparticle can be formed from any biocompatible hydrophobic polymer. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(hydroxyalkanoates); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers and blends thereof.

In some embodiments, the hydrophobic polymer nanoparticle is formed from a hydrophobic biodegradable polymer. In certain embodiments, the hydrophobic polymer nanoparticle is formed from an aliphatic polyester, such as poly(lactic acid), poly(glycolic acid), poly(lactic acid-co-glycolic acid), copolymers thereof, or blends thereof.

The hydrophobic polymer nanoparticle can be formed from a polymer to which one or more drugs are covalently attached. In one embodiment, the hydrophobic polymer nanoparticle is formed of a drug-polylactide or a drug-poly(lactic-co-glycolic acid) conjugate synthesized using living polymerization chemistry.

The hydrophobic polymeric nanoparticles can be prepared from any of the hydrophobic polymers or polymer conjugates using suitable methods for the preparation of polymeric nanoparticles, for example, using nanoprecipitation.

Preferably, the hydrophobic polymeric nanoparticles have an average particle size of between about 80 nm and about 400 nm, more preferably between about 80 nm and 250 nm, most preferably between about 80 nm and about 180 nm.

The one or more polymer drug conjugates can be assembled on the surface of the hydrophobic polymer nanoparticle by incubation of the one or more polymer-drug conjugates in a suspension of the hydrophobic polymeric nanoparticles in an appropriate solvent. The polymeric-drug conjugates will self-assemble onto the surface of the hydrophobic polymeric nanoparticle, forming nanoparticles containing a hydrophobic core, formed from hydrophobic polymer segments and hydrophobic polymer nanoparticle, and a hydrophilic shell composed of small nanoparticles formed from the hydrophilic polymer segments.

In some embodiments, the polymer-drug conjugates are covalently linked to the hydrophobic polymer nanoparticle subsequent to self-assembly.

C. Additional Drugs

In some cases, one or more additional drugs are dispersed in the hydrophobic core of the nanoparticles during nanoparticle formation.

In some embodiments, one or more anti-neoplastic agents, such as one or more of those described above, are dispersed in the nanoparticle during nanoparticle formation.

Drugs that are dispersed in the hydrophobic core during nanoparticle formation will generally be released as the hydrophobic core biodegrades. As a result, drugs dispersed in the hydrophobic core will primarily be released in the perivascular tumor tissue. In some embodiments, one or more drugs that target the development of tumor vasculature are dispersed in the nanoparticles during formation, and released in the perivascular tumor tissue. Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds; MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

In cases where it is desirable to render aberrantly proliferative cells quiescent in conjunction with the administration of one or more anti-neoplastic agents, hormones and steroids (including synthetic analogs) can also be dispersed in the hydrophobic polymer core. Examples of suitable hormones and steroids include 17-α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex, and combinations thereof.

In some embodiments, one or more diagnostic agents are dispersed in the nanoparticle during nanoparticle formation. In these embodiments, the diagnostic agent is selected, for example, to enhance imaging of the solid tumor. Exemplary diagnostic agents include paramagnetic molecules, fluorescent compounds, magnetic molecules, and radionuclides, x-ray imaging agents, and contrast agents.

IV. Pharmaceutical Formulations and Administration

Nanoparticles formed from polymer-drug conjugates can be combined with one or more pharmaceutically acceptable excipients to form a pharmaceutical formulation suitable for administration to an animal or human in need thereof. The one or more excipients can be incorporated during formation of the nanoparticles, for example by addition to one or more of the polymer-drug conjugate solutions. Alternatively, the one or more excipients can be combined with the nanoparticles after they are formed, when the nanoparticles are formulated into pharmaceutically acceptable compositions.

In some cases, the pharmaceutical formulation contains only one type of polymer-drug conjugate nanoparticles (i.e., the polymer-drug conjugate nanoparticles incorporated into the pharmaceutical formulation have the same composition). In other embodiments, the pharmaceutical formulation contains two or more different types of polymer-drug conjugate nanoparticles (i.e., the pharmaceutical formulation contains two or more populations of polymer-drug conjugate nanoparticles, wherein the populations of polymer-drug conjugate nanoparticles have different chemical compositions, different average particle sizes, and/or different particle size distributions).

The nanoparticles can be formulated for a variety of routes of administration and/or applications. For treatment of tumors, nanoparticles can be administered by injection intravenously, although nanoparticles may also be administered locally into and/or around the tumor, e.g., injection directly into the tumor or implantation.

Suitable dosage forms for parenteral administration include solutions, suspensions, and emulsions. Typically, nanoparticles will be suspended in sterile water, saline, phosphate buffered saline, or as an emulsion. Formulations for parenteral administration can contain one or more excipients, such as solvent, dispersing agents, pH modifying agents, buffers, preservatives, surfactants, emulsifying agents, and combinations thereof.

V. Indications

A pharmaceutical composition containing multistage nanoparticles formed from one or more polymer-drug conjugates can be administered to a subject to reduce the size of solid tumors, including benign and malignant tumors. In various embodiments the solid tumor to be treated is benign. In other embodiments the solid tumor to be treated is malignant and may be primary or secondary (metastatic). Solid tumors include, for example, adenocarcinomas, carcinomas, hemangiomas, liposarcomas, lymphomas, melanomas and sarcomas.

In general, solid tumors most suited to treatment using multistage nanoparticle formulations are highly vascularized tumors. In some embodiments, the tumor has a three-dimensional shape that results in cells in the interior of the tumor becoming hypoxic when the tumor reaches a diameter of about 2 mm. For tumors that are substantially spherical in shape, the term "diameter" is self-explanatory. For tumors that are substantially non-spherical, the term "diameter" herein refers to the size of the tumor in its shortest dimension.

The multistage nanoparticles formed from one or more polymer-drug conjugates can be administered to a subject to treat or prevent a cancerous or precancerous condition. In some embodiments, a formulation containing multistage nanoparticles is administered to a subject in need thereof in an effective amount deliver therapeutic levels of one or more drugs throughout a solid tumor in an effective amount to slow tumor growth, halt tumor growth, or decrease tumor size.

EXAMPLES

Example 1. Multistage Quantum Dot Gelatin Nanoparticles (QDGelNPs)

Materials and Methods
Reagents
Gelatin type A≈175 bloom from porcine skin, glutaraldehyde solution (Grade 1, 50%), N-Hydroxysulfosuccinimide Sodium salt (sulfo-NHS), N-(3-Dimethylaminopropyl)-N'-ethylcarbodiimide hydrochloride (EDC), methoxypolyethylene glycol amine 5,000 (mPEG-amine 5 kDa), agarose, hydrochloric acid fuming 37% TraceSelect, Nitric Acid>69.0% TraceSelect, and EDTA, Disodium Salt Dihydrate (EDTA) were purchased from Sigma-Aldrich. Acetone, Hepes, and 10×PBS Liquid Concentrate were purchased from EMD Chemicals. Calcium chloride, isopropyl alcohol, and glycine were obtained from Mallinckrodt Baker. ICP-OES cadmium standard 2% HNO3 (1,000 mg/liter) was purchased from Perkin-Elmer. Qdot 565 ITK amino (PEG) quantum dot and GIBCO Certified Heat-Inactivated FBS was obtained from Invitrogen. Block Casein in PBS was purchased from Thermo Scientific. Reagent grade deionized water used for ICP-OES experiments was purchased from Ricca Chemical. Water for all other experiments was obtained by using a Barnstead NANOpure DIamond Life Science UV/UF TOC water system (Thermo Fisher Scientific). Active Human Recombinant MMP-2 was purchased from EMD Chemicals. All reagents were used as obtained without further purification.

Synthesis of Gelatin Nanoparticles

Gelatin nanoparticles were prepared using a two-step desolvation method. Gelatin type A (0.625 g) was dissolved in 12.5 mL of deionized (DI) water at 40° C. Acetone (12.5 mL) was added to the solution at 6 mL/min. 1 min after the addition was completed, the supernatant containing the low molecular weight gelatin fraction was removed. DI water (12.5 mL) was added to the remaining precipitate and heated again to 40° C. until dissolution. Half the solution was removed, and the pH of the remaining half was adjusted to 2.7. Under constant stirring at 600 rpm and 40° C., 20.75 mL of acetone was added at 1 mL/min. After the acetone addition was completed, 30 µL of 50% glutaraldehyde solution (Grade I) diluted in 1 mL of acetone was added to the gelatin solution at 0.05 mL/min to cross-link the particles. Subsequently, the solution was kept at 40° C. and 600 rpm stir rate for 7.5 h. The acetone was then removed. The remaining solution was filtered through a 0.2-µm syringe filter. A 1 M glycine solution (0.2 mL) was added, and the solution was stored overnight at 4° C. A 1 mL solution of the gelatin particles was injected into a Superose 6 GL 10/300 column (GE Healthcare) for GFC purification. The peak eluting at the void volume was collected with 0.5-mL fractions. This purification procedure was repeated once more, and the first concentrated fractions from both GFC runs were combined.

Synthesis of Multistage Quantum Dot Gelatin Nanoparticles (QDGelNPs)

The 1 mL gelatin nanoparticle solution was combined with 20 µL of 8 µM PEG quantum dots (QDs). After stirring for 1 h and eventually changing the pH to 6, 0.4 mg (2.1 µmol) of EDC and 0.4 mg (1.9 µmol) of N-hydroxysulfosuccinimide (sulfo-NHS) was dissolved in 50 µL of DI water and then added to the gelatin nanoparticle/QD mixture. The reaction proceeded for 3 h. Afterward, a solution of mPEG amine 5 kDa (20 mg, ≈4 µmol) dissolved in 50 µL of DI water was added to the gelatin/QD solution. Then, an additional solution of EDC (0.4 mg) and sulfo-NHS (0.4 mg) was added. After 2 h, the pH was adjusted to 8 and stirring continued for 1 h. A 1 M glycine solution (50 µL) was added to quench the reaction. After 30 min, the resulting mixture was filtered through a 0.2-µm syringe filter and then purified by using GFC with the Superose 6 column. The peak eluting at the void volume was collected with 0.5-mL fractions and the first concentrated fraction was used for further experiments.

Collagen Gel Diffusion

Collagen hydrogels were prepared by mixing the following components in order on ice: 141.75 µL, of 8.6 mg/mL rat tail collagen I (354249; BD Biosciences), 3.8 µL, of 1 M sodium hydroxide, and 19.5 µL, of 0.17 M EDTA. The final concentration of collagen was 7.38 mg/mL and EDTA was 20 mM. After vortexing, the gel was added to partially fill a microslide capillary tube (Vitrocom no. 2540), then incubated overnight at 37° C. QDGelNPs (0.1 mg) were incubated with 230 ng of activated MMP-2 for 12 h in 50 mM Hepes, 2 mM $CaCl_2$. At the end of 12 h, EDTA was added to give a final concentration of 20 mM. A 20-µL mixture of the QDGelNPs either before or after incubation with MMP-2 and SilicaQDs was added into the capillary tube and placed in contact with the surface of the collagen gel. The concentration of the two particles and sensitivity of the avalanche photodiodes (APD) were adjusted so that both particles gave similar signal intensities. The sample was left in ≈295 K for 12 h and then imaged by using a multiphoton laser scanning microscope. Image analysis was performed by using ImageJ. The concentration profile for the QDGelNPs after cleaving was fitted to the following one-dimensional model to obtain the diffusion coefficient in the collagen gel:

$$C(x, t) \alpha \mathrm{erfc}\left(\frac{x}{2\sqrt{D_{eff}t}}\right),$$

where erfc is the complementary error function. The nonlinear curve fitting was performed by using fminsearch in Matlab. The diffusion coefficient ratio ($D/D_o$) was compared with reported values ($D/D_o$ has been found to be ≈0.35 for an 11.2 nm QD in 9.37 mg/mL collagen gel, and ≈0.95 for $D/D_o$ a ≈10 nm particle in 2.4 mg/mL collagen gel. By simple linear interpolation of these two values, $D/D_o=0.52$ was obtained for ≈10 nm NPs in 7.38 mg/mL collagen.

Intravital Multiphoton Microscopy

All animal procedures were done by following the guidelines of the Public Health Service Policy on Humane Care of Laboratory Animals and approved by the Institutional Animal Care and Use Committee of the Massachusetts General Hospital. Human fibrosarcoma HT-1080 cells were implanted in the dorsal skin of SCID mice for in vivo imaging. When tumors reached 5 mm in diameter, a 1 µL mixture of QDGelNPs and SilicaQDs (≈0.05 µL/min) was injected into the tumor at constant pressure by using a glass micropipette connected to a syringe filled with silicone oil.

Images were obtained with a custom-built multiphoton microscope by using a Ti:Sapphire laser (Mai-Tai Broadband; Spectra-Physics) at 900 nm, a 20× (0.5 N.A.; Olympus) water-immersion objective, and photon-counting photomultiplier tubes (H7421-40; Hamamatsu). Detection of QDGelNPs was performed via a 530DF100 emission filter and SilicaQDs via a 610DF75 emission filter. Collagen fibers were imaged with second-harmonic generation via a 450DF100 emission filter. The laser power was set to 500 mW. Three-dimensional image stacks containing 21 images of 5 µm thickness were obtained wherever fluorescence intensity from the injected particles was detected. A maximum intensity z projection of each colored stack generated a 2D image. Images of consecutive adjacent regions in the x and y directions were combined into a montage, generating a single image of the entire injection site.

The intensity profiles were extractedusing ImageJ and then normalized such that the backgrounds (a "dark" region from all three time-lapse images) had the same intensity. The background was subtracted, and the resulting profiles were fitted to the model for diffusing substance initially distributed uniformly through a sphere of radius a (34) to obtain the diffusion coefficient:

$$C(r, t) = \frac{1}{2}C_o\left\{\text{erf}\frac{a-r}{2\sqrt{Dt}} + \text{erf}\frac{a+r}{2\sqrt{Dt}}\right\} - \frac{C_o}{r}\sqrt{\frac{Dt}{\pi}}\left[\exp\left\{-\frac{(a-r)^2}{4Dt}\right\} - \exp\left\{\frac{(a+r)^2}{4Dt}\right\}\right],$$

where $C_o$ is the initial concentration in the sphere. It should be noted that the diffusion coefficient obtained in collagen gel was obtained at ≈295 K, whereas the in vivo experiment was measured at the slightly higher body temperature of ≈310 K.

Results

The QDGelNPs contained a gelatin core with amino-PEG QDs conjugated to the surface using 1-ethyl-3-[3-dimethylaminopropyl]carbodiimide hydrochloride (EDC)/sulfo-NHS coupling chemistry. Another layer of 5 kDa polyethylene glycol (PEG) was conjugated to the surface of the gelatin nanoparticles to confer long blood circulation time. X-ray photoelectron spectroscopy (XPS) was used to determine the presence of PEG chains on the QDGelNPs surface. Dynamic light scattering (DLS) of the QDGelNPs before and after PEGylation (but before purification) indicate an increase in diameter from 78.3±0.2 nm to 93.7±0.5 nm. DLS of the final structure after purification and size selection using gel filtration chromatography (GFC) revealed a single particle distribution with a hydrodynamic diameter of 97.9±2.1 nm and a polydispersity of 41.2%. This value agreed well with the average diameter of 99±1 nm estimated from scanning electron microscopy (SEM). Inductively coupled plasma optical emission spectroscopy (ICP-OES) determined a concentration of 15 pmol of QDs per mg of QDGelNPs. The QDGelNPs showed excellent colloidal stability; their diameter by DLS remained nearly unchanged while in storage at ≈4° C. over 48 days—from 95.7±4.1 nm on day 1 to 101.1±2.5 nm on day 48.

The initial 100 nm NPs and the released 10 nm NPs were both designed to have a neutral surface charge, ensuring the difference in transport before and after cleaving is only a result of size change. In addition, it is known in the art that neutral particles are optimal for diffusion in the interstitial matrix. The ζ potential of the ≈100 nm QDGelNPs at pH 7.5 was −6.29±0.22 mV and at pH 6 was −5.00±0.12 mV. The ζ potential of the ≈10 nm QDs used for the second stage NP was −5.13±0.16 mV at pH 7.5 and −4.36±0.17 mV at pH 6. These results confirm the charge neutrality of both particles in the pH range found in normal tissues and solid tumors.

Figure 4:
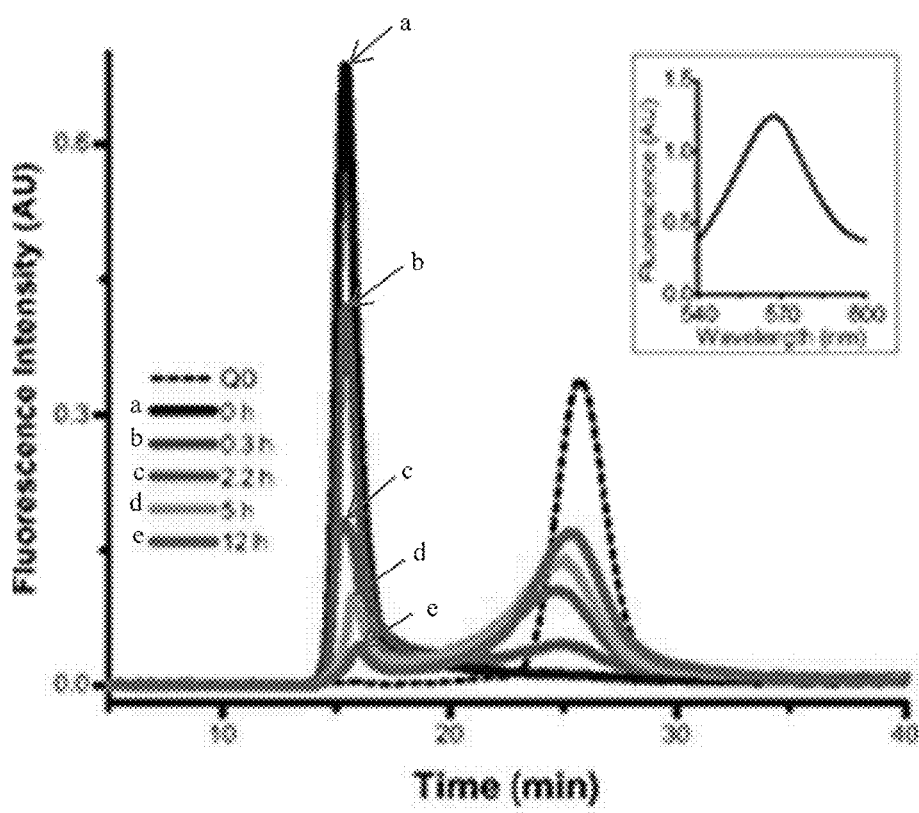
FIG. 4 is an overlayed plot of GFC chromatograms showing release from multistage quantum dot gelatin nanoparticles (QDGelNPs) at various times after incubation with MMP-2. The gel filtration chromatograms (GFCs) plot the fluorescence intensity (in arbitrary units) as a function of elution time (in minutes) following incubation with MMP-2 for 0 hours, 0.3 hours, 2.2 hours, 5 hours, and 12 hours (top to bottom traces at time≈15 minutes). For comparison, the dotted trace shows the GFC of the QD control. The fluorescence signal was collected at 565 nm. Fluorescence spectrum of the peak at void volume for 2.2 hours cleaving time shows that the signal originates from QDs on the QDGelNPs.

The ability of MMP-2 to change the size of QDGelNPs in vitro was investigated using GFC. GFC chromatograms using fluorescence detection (ex: 250 nm, em: 565 nm) were obtained from incubation of 0.1 mg of QDGelNPs with 230 ng (0.16 μM) of MMP-2 at 37° C. (See FIG. 4). The extracellular concentration of MMP-2 in HT-1080 (human fibrosarcoma) xenograft tumor tissue in vivo has been previously estimated to be ≈1 mM, significantly higher than the concentration used in our in vitro experiment.

Figure 5A:
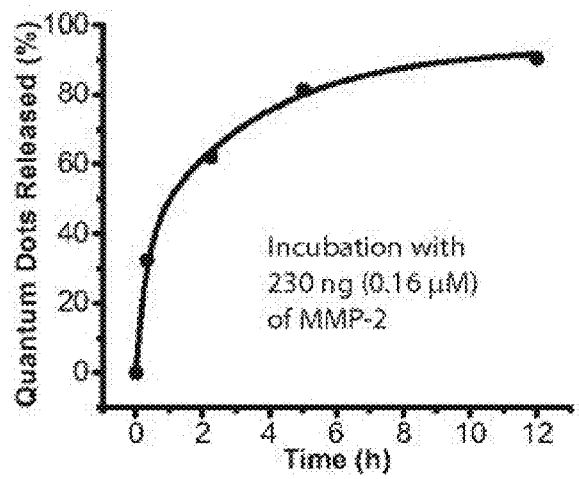
FIGS. 5A and 5B are plots demonstrating the kinetics of MMP-2-induced quantum dot (QD) release from multistage quantum dot gelatin nanoparticles (QDGelNPs).
Figure 5B:
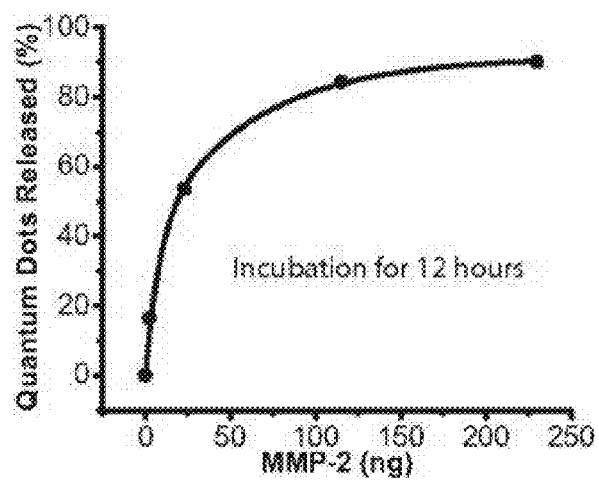

The QDGelNPs initially eluted at the GFC column's void volume but after incubation with MMP-2 for various times up to 12 hours, the peak shifted to a longer elution time corresponding to the smaller size of individual QDs, whereas incubation with 50% FBS showed no such shift. 50% of the QDs were released in ≈1.5 h and the percent of freed QDs saturated at ≈90% (FIG. 5A), regardless of longer incubation times or addition of more MMP-2. We repeated this experiment with the incubation time kept constant at 12 h but the amount of MMP-2 was varied (FIG. 5B). Under this condition, only ≈25 ng of MMP-2 was necessary to release 50% of the QDs. These results demonstrated the MMP-2 triggered size change occurred in an efficient manner.

The ability of the released QDs diffuse optimally in the interstitial matrix was then investigated. Specifically, we wanted to confirm that residual gelatin/glutaraldehyde on the particle surface, imparted by cleavage of the gelatin NPs, does not lead to extraneous binding interactions or significant size increase. To investigate this possibility, fluorescence correlation spectroscopy (FCS) was used to directly measure the hydrodynamic diameter/diffusion coefficient of the QDs before and after cleaving the gelatin core. The hydrodynamic diameter by FCS before cleaving was 81.1±2.3 nm (D=5.6±0.2×10$^{-8}$ cm$^2$·s$^{-1}$), which is consistent with the DLS measurement of 90.9±1.3 nm for this batch. After MMP-2 digestion, the hydrodynamic diameter decreased to 9.7±0.3 nm (D=4.7±0.2×10$^7$ cm$^2$·s$^{-1}$), which is the size of individual QDs, indicating the size increase of the released QDs from gelatin/glutaraldehyde fragments was negligible.

The effect of the particle size change on diffusive transport in dense collagen environments resembling those in solid tumors was then observed using GFC and FCS. To simulate the interstitial matrix of a solid tumor, we prepared a collagen gel in a capillary tube at 0.74% (7.4 mg/mL) concentration, similar to the reported estimate of 9.0±2.5 mg/(mL interstitial matrix) for interstitial collagen in both human colon adenocarcinoma (LS174T) and murine mammary carcinoma (MCaIV) implanted in mouse dorsal chambers. The collagen gel penetration of the QDGelNPs before and after cleaving with MMP-2 was compared with a noncleavable, PEGylated, and QD-coated silica nanoparticles control (Diam.=105.6±0.8 nm, ζ potential at pH 7.5=−3.9±0.2 mV) designed to behave like QDGelNPs before cleaving. A mixture of SilicaQDs and QDGelNPs (before or after cleaving) were placed in contact with the gel and incubated for 12 hours. Infiltration of both particles into the collagen was determined using multiphoton microscopy with simultaneous second-harmonic generation (SHG) imaging of fibrillar collagen. The SilicaQDs and QDGelNPs before cleaving both had negligible penetration and were excluded from the collagen matrix. However, after cleavage of QDGelNPs with MMP-2, the freed QDs were able to penetrate over a millimeter into the gel. By fitting the concentration profile of the cleaved QDGelNPs to a one-dimensional diffusion model, a diffusion coefficient of 2.3× 10$^{-7}$ cm$^2$·s$^{-1}$, the same diffusion coefficient obtained for individual QDs in the collagen gel before conjugation to the gelatin NP, was obtained. The resulting diffusion coefficient ratio (D/D$_o$, where D$_o$ is diffusion coefficient of freed QDs in solution obtained by FCS) in the collagen matrix is 0.49. This value agrees well with the expected value for D/D$_o$ of ≈0.52 derived from previous reports. This result indicates that the diffusion coefficient of released QDs in dense collagen increases to that of ≈10 nm particles and any residual gelatin/glutaraldehyde fragments remaining on the surface do not impede their diffusion.

To examine whether tumor secreted MMP-2 can change the size of QDGelNPs in vivo, QDGelNPs and SilicaQDs were intratumorally coinjected into a HT-1080 tumor implanted in the dorsal skin-fold window chamber of severe combined immunodeficient (SCID) mice. The HT-1080 tumor model was selected because of its reported high MMP-2 activity, which we confirmed by in situ gelatin zymography on a tumor tissue section. Multiphoton microscopy revealed a marked increase in QDGelNPs penetration into surrounding tumor tissue as compared with the non-cleavable SilicaQDs control, confirming a substantial enhancement in interstitial transport associated with size change. At 6 hours postinjection, the QDGelNPs had penetrated up to ≈300 μm from the injection site while the SilicaQDs control exhibited little or no dissemination from its initial location. The concentration profile was fitted to a model for substances diffusing from a spherical source to obtain an effective diffusion coefficient of $\approx 2.2 \times 10^{-8}$ cm$^2 \cdot$s$^{-1}$ inside the tumor. This value is ≈10% the diffusion coefficient obtained in the collagen gel, which can be explained by the increased time needed to cleave the particles, the tortuosity of the interstitial space induced by cellular obstacles (35), and the possibly higher collagen concentration in the HT-1080 tumor than in the gel.

The QDGelNPs' blood half-life ($t_{1/2\beta}$) was measured to determine if the QDGelNPs are rapidly removed from circulation by the reticuloendothelial system. A mixture of the QDGelNPs and SilicaQDs was systemically administered to non-tumor bearing mice by retro-orbital injection. The decrease in fluorescence from both particles in the blood over time was measured. The SilicaQDs exhibited a blood half-life of 12.9±2.4 h, whereas the QDGelNPs had a half-life of 22.0±3.4 h. The difference in the half-lives may be due to variations in the QDGelNPs' surface chemistry that make it less immunogenic compared with SilicaQDs. These results established that QDGelNPs possess both the long circulation half-life and large 100-nm size necessary for preferential extravasation from the leaky regions of the tumor vasculature as well as the deep interstitial penetration of a 10-nm particle required for delivery to the tumor's poorly accessible regions.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A polymer-drug conjugate defined by Formula I or Formula IV

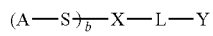

Formula I or

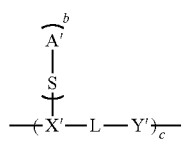

Formula IV wherein

A is, independently for each occurrence, a therapeutic, prophylactic or diagnostic agent;

S is absent, or is a spacer group;

X is a hydrophilic polymer segment comprising a graft copolymer, wherein the graft copolymer comprises a polymeric backbone comprising a poly(amino acid), wherein the backbone is functionalized by one or more hydrophilic polymeric side chains;

L is absent, or is a hydrolysable or enzymatically cleavable linking group;

Y is a hydrophobic polymer segment;

b and c are independently integers between 1 and 100,

A' is, independently for each occurrence, anti-neoplastic drug;

X' is a hydrophilic polymer segment comprising a graft copolymer, wherein the graft copolymer comprises a polymeric backbone comprising a poly(amino acid), wherein the backbone is functionalized by one or more hydrophilic polymeric side chains, wherein the graft copolymer has a grafting ratio of between about 1.5% and 60%;

Y' is a poly(alkylene oxide) or copolymer thereof; and wherein the conjugates are capable of forming nanoparticles having a diameter between about 80 nm and about 500 nm, having hydrophilic polymer on the outer surface and a hydrophobic polymer core, and wherein the nanoparticles release smaller nanoparticles upon exposure to hydrolysis or an enzyme in a tumor microenvironment.

2. The conjugate of claim 1, wherein A is a small-molecule anti-neoplastic agent.

3. The conjugate of claim 2, wherein A is an anthracycline or a topoisomerase inhibitor.

4. The conjugate of claim 1, wherein Y comprises an aliphatic polyester.

5. The conjugate of claim 1, wherein Y is selected from the group consisting of poly(lactide), poly(glycolide), poly(caprolactone), and copolymers thereof.

6. The conjugate of claim 1, wherein the graft copolymer is functionalized by one or more poly(alkylene glycol) side chains.

7. The conjugate of claim 6, wherein the poly(alkylene glycol) side chains comprise polyethylene glycol) or copolymers thereof.

8. The conjugate of claim 1, wherein the poly(amino acid) is selected from the group consisting of polyglutamic acid, polyaspartic acid, polyserine, polylysine, copolymers thereof, and combinations thereof.

9. The conjugate of claim 1, wherein the hydrolysable functional group is selected from the group consisting of an ester, an amide, and a glycosidic bond.

10. The conjugate of claim 1, wherein the enzymatically cleavable group is an oligo- or poly(peptide) cleavable by matrix metalloproteinase-2 (MMP-2), matrix metalloproteinase-9 (MMP-9), Cathepsin B, autotaxins, and combinations thereof.

11. A polymer drug conjugate defined by Formula II

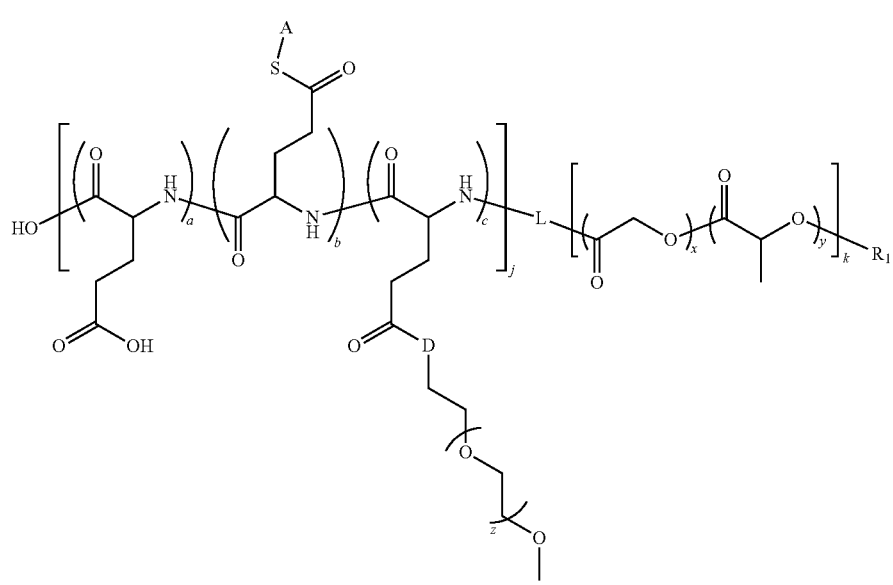

Formula II wherein
  A is a drug;
  S is absent, or is a spacer group;
  L is absent, or is a linking group;
  D is, independently for each occurrence, O, S, or $NR_1$;
  $R_1$ is H or a $C_1$-$C_{12}$ alkyl group optionally containing between one and six oxygen heteroatoms;
  a, b, and c are each, independently, an integer between 1 and 1000;
  x and y are each, independently, an integer between 1 and 1000;
  z is, independently for each occurrence, an integer between 1 and 1000; and
  j and k are each, independently, an integer between 1 and 1000.

12. A polymer drug conjugate defined by Formula III

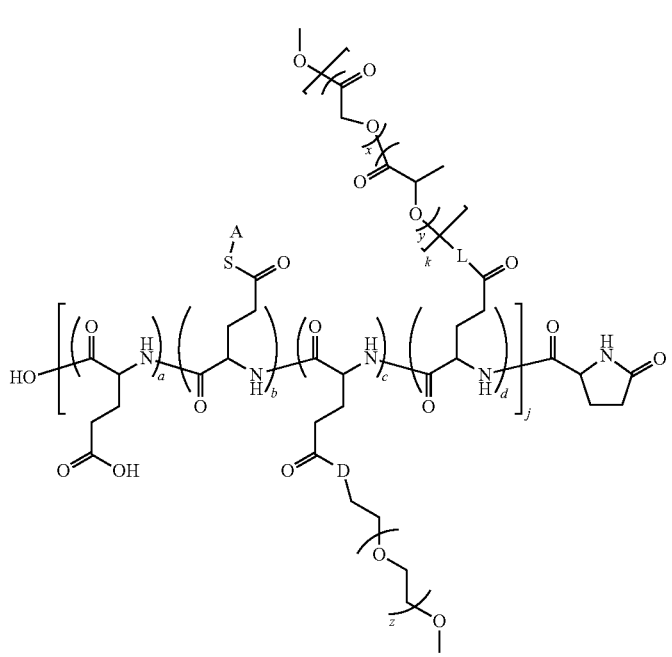

Formula III wherein
  A is a drug;
  S is absent, or is a spacer group;
  L is absent, or is a linking group;

D is, independently for each occurrence, O, S, or $NR_1$;
$R_1$ is H or a $C_1$-$C_{12}$ alkyl group optionally containing between one and six oxygen heteroatoms;
a, b, c, and d are each, independently, an integer between 1 and 1000;
x and y are each, independently, an integer between 1 and 1000;
z is, independently for each occurrence, an integer between 1 and 1000; and
j and k are each, independently, an integer between 1 and 1000.

13. A polymer drug conjugate defined by Formula V

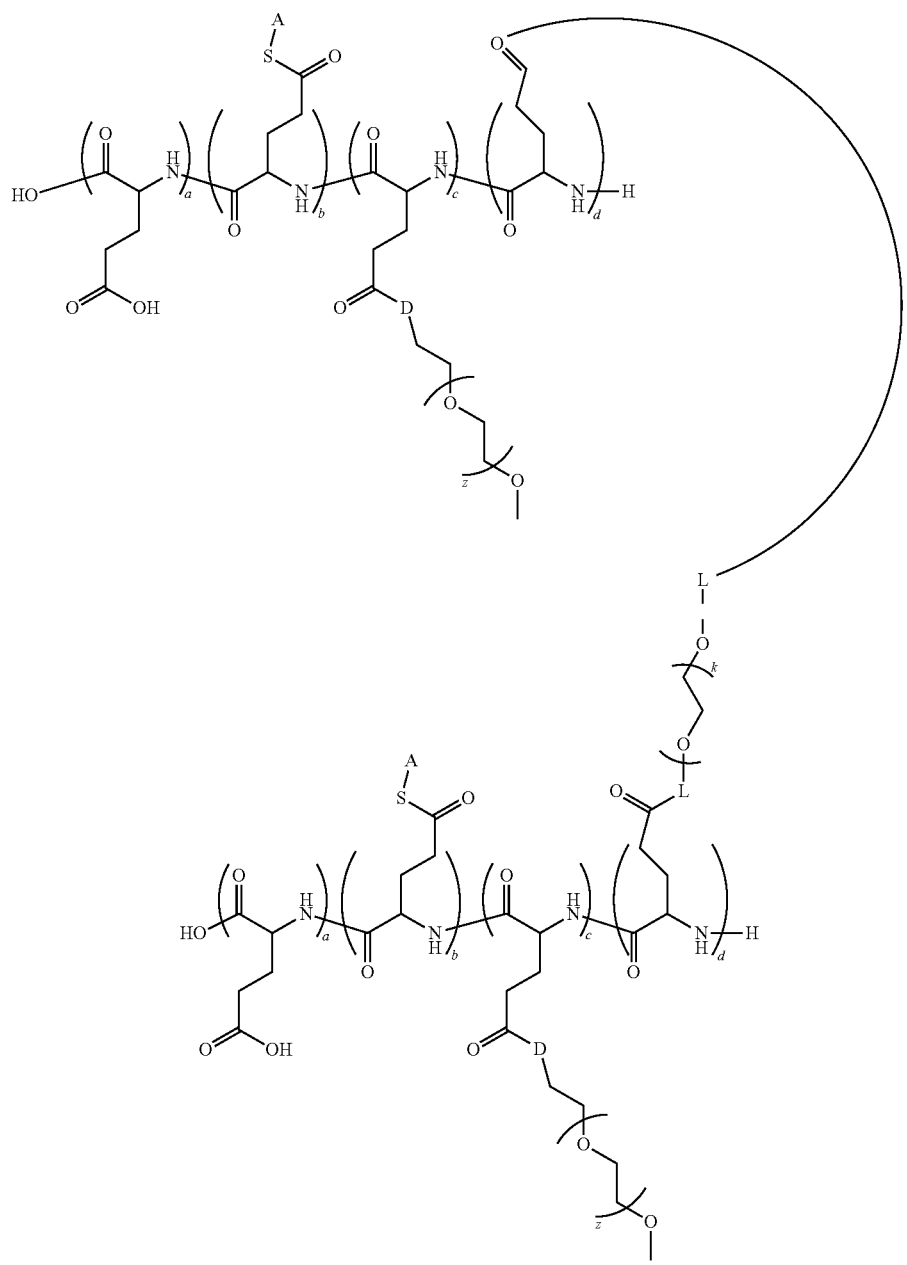

Formula V wherein
A is a drug;
S is absent, or is a spacer group;
L is absent, or is a linking group;
D is, independently for each occurrence, O, S, or $NR_1$;
$R_1$ is H or a $C_1$-$C_{12}$ alkyl group optionally containing between one and six oxygen heteroatoms;
a, b, c, and d are each, independently, an integer between 1 and 1000;
z is, independently for each occurrence, an integer between 1 and 1000; and
k is an integer between 1 and 1000.

14. The polymer-drug conjugate of claim 1, formed into a nanoparticle or in a nanoparticle.

15. The polymer-drug conjugate claim 14, wherein the nanoparticle has an average particle size of between 80 nm and 500 nm.

16. The nanoparticles defined by claim 15, wherein the nanoparticles have an average particle size of between 100 nm and 200 nm.

17. A method of treating a solid tumor comprising administering to a subject in need thereof a formulation comprising the nanoparticles of claim 14.

18. The method of claim 17, wherein the formulation is administered by intravenous injection.

19. The method of claim 17, wherein the formulation is administered by injection into the tumor, injection around the tumor, or combinations thereof.

20. The method of claim 17, wherein the solid tumor is selected from the group consisting of adenocarcinomas, carcinomas, hemangiomas, liposarcomas, lymphomas, melanomas, and sarcomas.

21. The method of claim 17, wherein the formulation is administered in an effective amount to slow tumor growth, halt tumor growth, or decrease tumor size.

22. The method of claim 17, wherein the tumor vasculature is more permeable and/or of a larger diameter than the vasculature in normal tissue, and the nanoparticles have a mean average diameter larger than the average diameter of the vasculature of the normal tissue and smaller than the diameter of the tumor vasculature.

23. The conjugate of claim 1, wherein the one or more polymeric side chains have the same or different polymeric compositions.

24. The conjugate of claim 1, wherein the agent is released when the linker L is cleaved.

25. The conjugate of claim 24 wherein A is an antineoplastic agent.

26. The conjugate of claim 1, wherein is selected from the group consisting of poly(ethylene glycol) and copolymers thereof.

* * * * *

UNITED STATES PATENT AND TRADEMARK OFFICE
CERTIFICATE OF CORRECTION

PATENT NO. : 9,919,059 B2
APPLICATION NO. : 14/102118
DATED : March 20, 2018
INVENTOR(S) : Wong et al.

Page 1 of 1

It is certified that error appears in the above-identified patent and that said Letters Patent is hereby corrected as shown below:

In the Specification

In Column 1, Lines 11-17, delete:
"This invention was made with government support under Agreement Nos. R01-CA126642, R01-CA085140, R01-CA115767, R01-CA080124, and R01-CA096915 awarded by the National Institutes of Health, and Agreement No. W81XWH-10-1-0016 awarded by the U.S. Department of Defense Breast Cancer Research Program. The government has certain rights in the invention."

And insert:
-- This invention was made with government support under R01 CA126642,U54 CA151884,R01 CA085140,R01 CA115767, and R01 CA080124 awarded by the National Institutes of Health, and W81XWH-10-1-0016 awarded by the Defense Health Agency, Medical Research and Development Branch. The government has certain rights in the invention. --

Signed and Sealed this
Sixteenth Day of December, 2025

John A. Squires
*Director of the United States Patent and Trademark Office*